(12) United States Patent
Bromberg et al.

(10) Patent No.: US 7,208,134 B2
(45) Date of Patent: Apr. 24, 2007

(54) BIOPROCESSES ENHANCED BY MAGNETIC NANOPARTICLES

(75) Inventors: Lev E. Bromberg, Swampscott, MA (US); T. Alan Hatton, Sudbury, MA (US); Daniel I. C. Wang, Newton, MA (US); Jin Yin, Somerville, MA (US); Bernat Olle, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 123 days.

(21) Appl. No.: 11/017,433

(22) Filed: Dec. 20, 2004

(65) Prior Publication Data

US 2006/0040388 A1 Feb. 23, 2006

Related U.S. Application Data

(60) Provisional application No. 60/530,862, filed on Dec. 18, 2003.

(51) Int. Cl.
*B32B 7/00* (2006.01)
*B32B 27/04* (2006.01)
*C01G 49/00* (2006.01)
*H01F 1/00* (2006.01)

(52) U.S. Cl. .................. 423/592.1; 423/632; 423/633; 423/594.19; 428/357; 428/379; 428/380; 428/396; 428/403; 428/407; 977/773; 977/775; 977/811; 252/62.51 R; 252/62.54; 252/62.56; 204/157.42; 427/212; 427/215; 427/220

(58) Field of Classification Search .............. 423/632, 423/633, 594.19, 592.1; 428/835.7, 835.8, 428/357, 379, 380, 396, 403, 407; 977/773, 977/775, 811; 252/62.51 R, 62.54, 62.56; 204/157.42; 427/212, 215, 220
See application file for complete search history.

(56) References Cited

U.S. PATENT DOCUMENTS

| | | | |
|---|---|---|---|
| 3,764,540 A | 10/1973 | Khalafalla et al. | 252/62.55 |
| 3,843,540 A | 10/1974 | Reimers et al. | 252/62.52 |
| 4,094,804 A | 6/1978 | Shimoiizaka | 252/62.52 |
| 4,867,910 A * | 9/1989 | Meguro et al. | 252/62.56 |
| 5,147,573 A | 9/1992 | Chagnon | 252/62.52 |
| 5,314,679 A | 5/1994 | Lewis et al. | 424/9 |
| 5,456,986 A | 10/1995 | Majetich et al. | 428/403 |
| 5,902,569 A | 5/1999 | Oshima et al. | |
| 6,150,181 A | 11/2000 | Halbreich et al. | 436/526 |
| 6,162,532 A | 12/2000 | Black et al. | 428/323 |
| 6,291,070 B1 | 9/2001 | Arpac et al. | |
| 6,353,037 B1 | 3/2002 | Thunhorst et al. | |
| 6,514,481 B1 | 2/2003 | Prasad et al. | 424/9.32 |
| 6,517,802 B1 * | 2/2003 | Xiao et al. | 423/592.1 |
| 6,620,627 B1 | 9/2003 | Liberti et al. | 436/526 |
| 6,623,982 B1 | 9/2003 | Liberti et al. | 436/526 |
| 6,730,395 B2 | 5/2004 | Covington | 428/323 |
| 6,767,635 B1 | 7/2004 | Bahr et al. | 428/402 |
| 6,780,343 B2 * | 8/2004 | Hata et al. | 252/62.52 |
| 6,800,271 B2 * | 10/2004 | Sinha et al. | 423/632 |
| 2002/0034666 A1 | 3/2002 | Kiely | 428/694 TS |
| 2002/0074541 A1 | 6/2002 | Covington | 257/9 |
| 2003/0059604 A1 | 3/2003 | Hattori et al. | 428/329 |
| 2003/0157371 A1 | 8/2003 | Ihara et al. | 428/694 BA |
| 2003/0190475 A1 | 10/2003 | Carpenter et al. | 428/403 |
| 2003/0203507 A1 | 10/2003 | Liberti et al. | 436/526 |
| 2004/0013907 A1 | 1/2004 | Waki et al. | 428/694 BA |
| 2004/0134565 A1 | 7/2004 | Sun et al. | 148/105 |
| 2004/0137220 A1 | 7/2004 | Tsuchiya et al. | 428/328 |
| 2004/0174917 A1 | 9/2004 | Riman et al. | |
| 2004/0208825 A1 | 10/2004 | Carpenter et al. | 424/9.36 |
| 2005/0025971 A1 | 2/2005 | Cho et al. | 428/403 |

OTHER PUBLICATIONS

Bucak, S. et al., "Protein Separations Using Colloidal Magnetic Nanoparticles", *Biotechnol. Prog.*, 19:477-484 (2003).
Cushing, B. L., et al., "Recent Advances in the Liquid-Phase Syntheses of Inorganic Nanoparticles", *Chem. Rev.*, 104:3893-3946 (2004).
Deng, Y. et al., "Preparation of magnetic polymeric particles via inverse microemulsion polymerization process", *Journ. of Magnetism and Magnetic Materials*, 257:69-78 (2003).
Dixon, D. D. et al., "Fluorocarbons: properties and syntheses", *Federation Proceedings*, 34(6):1444-1448 (May 1975).
Elaïssari, A. et al., "Hydrophilic magnetic latex for nucelic acid extraction, purification and concentration", *Journ. of Magnetism and Magnetic Materials*, 255:127-133 (2001).
Flaim, S. F., "Pharmacokinetics and Side Effects of Perfluorocoarbon-Based Blood Substitutes", *Art. Cells, Blood Subs., and Immob. Biotech.*, 22(4):1043-1054 (1994).
Fu, L. et al., "Self-assembled (SA) bilayer molecular coating on magnetic nanoparticles", *Applied Surface Science*, 181:173-178 (2001).
Furusawa, K. et al., "Synthetic process to control the total size and component distribution of multilayer magnetic composite particles", *Colloid Polym. Sci.*, 272:1104-1110 (1994).
Gupta, P. K., et al., "Magnetically Controlled targeted Micro-Carrier Systems", *Life Sci.*, 44:175-186 (1989).

(Continued)

*Primary Examiner*—Timothy C. Vanoy
(74) *Attorney, Agent, or Firm*—Dana M. Gordon; Foley Hoag LLP

(57) ABSTRACT

One aspect of the present invention relates to magnetic nanoparticles colloidally stabilized in aqueous milieu by association with an organic phase. The organic phase may be either a fluorinated polymer or an organic hydrocarbon bilayer, wherein the two layers are chemically bonded to each other. The stabilized particles are further non-toxic and provide useful enhancements in bioprocesses. Another aspect of the present invention relates to compositions comprising an oxygen-dissolving fluid vehicle and surface modified, nanometer-sized magnetic particles. The inventive compositions have utility in a wide range of applications, but are particularly suitable for use as recyclable oxygen carriers, separation and purification vehicles, and bioprocessing media, including fermentation processes.

36 Claims, 34 Drawing Sheets

OTHER PUBLICATIONS

Haik, Y. et al., "Development of magnetic device for cell separation", *Journ. of Magnetism and Magnetic Materials*, 194:254-261 (1999).

Hemmi, T., "Trend of Magnetic Fluids and Its Application", *Japanese Journal of Tribology*, 37(2):149-158 (1992).

Kawaguchi, H. et al., "Modification and functionalization of hydrogel microspheres", *Colloids and Surfaces—Physicochemical and Engineering Aspects*, 109:147-154 (1996).

Krafft, M. P. et al., "The Design and Engineering of Oxygen-Delivering Fluorocarbon Emulsions", *Submicronic Emulsions in Drug Targeting and Delivery*, Harwood Academic Publ., Amsterdam, S. Benita, Editor, 235-333 (1998).

Leslie-Pelecky, D. L., "Magnetic Properties of Nanostructured Materials", *Chem. Mater.*, 8:1770-1783 (1996).

Lowe, K. C., "Properties and Biomedical Applications of Perfluorochemicals and Their Emulsions", In *Organofluorine Chemistry: Principles and Commercial Applications*, 555-573 (1994).

McMillan, J. D. et al., "Mechanisms of Oxygen Transfer Enhancement during Submerged Cultivation in Perfluorochemical-in-Water Dispersions", *Annals New York Acad. of Sci.*, 589:283-300 (1990).

Meza, M., "Application of Magnetic Particles in Immunoassays", *Scienctific and Clinical Applications of Magnetic Carriers*, Plenum Press, New York, Häfeli et al, eds., 303-309 (1997).

Moeser, G. D. et al., "Water-Based Magnetic Fluids as Extractants for Synthetic Organic Compounds", *Ind. Eng. Chem. Res.*, 41:4739-4749 (2002).

Nuzzo, R. G. et al., "Fundamental Studies of the Chemisoption of Organosulfur Compounds on Au(111). Implications for Molecular Self-Assembly on Gold Surfaces", *J. Am. Chem. Soc.*, 109:733-740 (1987).

Reiss, J. G. et al., "Perfluoro Compounds as Blood Substitutes", *Angewandte Chemie*, 17(9):621-700 (Sep. 1978).

Sandroff, C. J. et al., "Surface-Enhanced Raman Study of the Solid/Liquid Interface: Conformational Changes in Adsorbed Molecules", *Chemical Physics Letters*, 96(5):547-551 (Apr. 22, 1983).

Santra, S. et al., "Synthesis and Characterization of Silica-Coated Iron Oxide Nanoparticles in Microemulsion: The Effect of Nonionic Surfactants", *Langmuir*, 17:2900-2906 (2001).

Sauzedde, F. et al., "Hydrophilic magnetic polymer latexes. 1. Adsorption of magnetic iron oxide nanoparticles onto various cationic latexes", *Colloid Polym. Sci.*, 277:846-855 (1999).

Sauzedde, F. et al., "Hydrophilic magnetic polymer latexes. 2. Encapsulation of adsorbed iron oxide nanoparticles", *Colloid Polym. Sci.*, 277:1041-1050 (1999).

Saynattjoki, M. et al., "Magnetic Fluids in Sealing and Lubrication—A State of the Art Review", *Synthetic Lubrication*, 10:119-131 (1993).

Shen, L. et al., "Aqueous magnetic fluids stabilized by surfactant bilayers", *Journ. of Magnetism and Magnetic Materials*, 194:37-44 (1999).

Smart, B. E., "Characteristics of C-F Systems", *Organofluorine Chemistry: Principles and Commercial Applications*, 57-82 (1994).

Sugibayashi, K. et al., "Drug-carrier Property of Albumin Microspheres in Chemotherapy. I. Tissue Distribution of Microsphere-entrapped 5-Fluorouracil in Mice", *Chem. Pharm. Bull.*, 23(12):3433-3434 (1977).

Tartaj, P. et al., "Advances in magnetic nanoparticles for biotechnology applications", *Journ. of Magnetism and Magnetic Materials*, 290-291:28-34 (2005).

Ulman, A. et al., "On the Formation of Ordered Two-Dimensional Molecular Assemblies", *Langmuir*, 8:894-897 (1992).

Weisbecker, C. S. et al., "Molecular Self-Assembly of Aliphatic Thiols on Gold Colloids", *Langmuir*, 12:3763-3772 (1996).

International Search Report dated May 26, 2005.

\* cited by examiner $$X_{max} = X_0 e^{\mu t}$$

$$N_A = X_{max}\mu/Y_{C/O} \sim 425 \text{ mmole } O_2/L \text{ hr}$$

$$= k_L a(C^* - C_L) \sim 105 \text{ mmole } O_2/L \text{ hr}$$

$(D_{O2}/\delta)$    Bubble Size    Depends on Henry's Law Constant $$\tau_D = \frac{\ell^2}{D} = \frac{\Gamma^2}{c^2 D} \qquad \ell = \frac{\Gamma}{c}$$

$$\tau_D(\phi_p = 2\% \, w/v) = \frac{\left(1.98 \cdot 10^{-10} \, \frac{cm^2}{mol}\right)^2}{\left(3.94 \cdot 10^{-6} \, \frac{mol}{cm^3}\right)^2 2.4 \cdot 10^{-7} \, \frac{cm^2}{s}} = 10 \, m \, sec$$

Relevant time scales for cell free system and fermentation system are ~1 sec

BIOPROCESSES ENHANCED BY MAGNETIC NANOPARTICLES

RELATED APPLICATIONS

This application claims the benefit of priority to U.S. Provisional Patent Application Ser. No. 60/530,862, filed Dec. 18, 2003; the entirety of which is hereby incorporated by reference.

BACKGROUND OF THE INVENTION

Magnetic nanoparticles have been extensively studied. D. L. Leslie-Pelecky and R. D. Rieke, *Chem. Mater.*, 1996, 8, 1770. They are known to change their magnetic properties from ferromagnetic to superparamagnetic below a critical size. Ultrafine particles of magnetic oxides may be used for preparing liquid magnets or ferrofluids. M. Saynattjoki and K. Holmberg, *Synthetic Lubrication*, 1993, 10, 119; T. Hemmi, *Japanese Journal of Tribology*, 1992, 37, 155. Generally, the particles are dispersed in water or non-polar solvents (hydrocarbons). Because they are used in numerous types of devices requiring liquid flows, the dispersions need to have high stability with respect to agglomeration and sedimentation in order to be able to flow and to respond quickly and without magnetic hysteresis to the imposition of an external magnetic field. D. L. Leslie-Pelecky and R. D. Rieke, *Chem. Mater.*, 1996, 8, 1770; M. Saynattjoki and K. Holmberg, *Synthetic Lubrication*, 1993, 10, 119; T. Hemmi, *Japanese Journal of Tribology*, 1992, 37, 155; U.S. Pat. No. 5,147,573; U.S. Pat. No. 4,094,804; U.S. Pat. No. 3,764,540; U.S. Pat. No. 3,843,540.

Various techniques for preparing particles in solution are known in the art. The synthesis procedures in aqueous solution show difficulties in the control of the particle size and size distribution, as well as the methods of prolonged milling. Other techniques, such as gas evaporation or sputtering, require complex equipment and are plagued by their high costs. The drawback of the methods commonly used is the poor particle dimensional control, both in size and size distribution. In particular, aggregation phenomena can occur in these processes.

Magnetic nanoparticles provide for required colloidal stability in aqueous environments and are of special interest because of their important technological applications in disparate fields ranging from magnetic recording to biodiagnostics and therapeutics. Surfactant-coated magnetic nanoparticles of metal oxide have been reported. A. Ulman, R. P. Scaringe, *Langmuir*, 1992, 8, 894. Works describing the synthesis and characterization of self-assembled multiple coatings on nanoparticles is an emerging field important in light of the renewed significance of nanostructured materials and devices. Magnetite stabilization using bilayer coatings has been described by Hatton et al. L. Shen, P. E. Laibinis, T. A. Hatton., *J. Magn. Matter.*, 1999, 194, 37.

Coating of surfaces can often change the intrinsic physical-chemical properties of the nanoparticles. The coatings on the surface of nanostructured powders are of great interest, because the coatings alter the charge, functionality, and reactivity of the surface, and enhance the stability and dispersibility of the nanoparticles in water-prepared monolayer and bilayer surfactant coatings on magnetite ($Fe_3O_4$) nanoparticles using the self-assembly method. C. S. Weisbecker, M. V. Merrit, G. M. Whitesides, *Langmuir*, 1996, 12, 3763; R. G. Nuzzo, B. R. Zegarski, L. H. Dubois, *J. Am. Chem. Soc.*, 1987, 109, 733; C. J. Sandorff, S. Garoff, K. P. Leung *Chem. Phys. Lett.*, 1983, 96, 547; L. Fu, V. P. Dravid, D. L. Johnson, *Appl. Surf. Sci.*, 2001, 181, 173. Reactions between magnetic nanoparticles and various groups via covalent, ionic, coordination, van der Waals, and/or hydrogen bonds are well-known in the art. M. Aoyagi, H. Sato, K. Yagi, N. Fukuda, S. Nishimoto, *Colloid & Polymer Science*, 2001, 279, 46; Pan, H. K., Meagher, A., Pineri, M., Knapp, G. S., Cooper, S. L. J., *Chem. Phys.*, 1985, 82(3), 1529; Xulu, P. M.; Filipcsei, G.; Zrinyi, M., 2000, 33(5), 1716; Shchukin, D. G., Radtchenko, I. L., Sukhorukov, G. B., *J. Phys. Chem. B.*, 2003; 107(1), 86; Shen, L., Laibinis, P. E., Hatton, T. A., Langmuir, 1999, 15(2), 447; Shen, L., Stachowiak, A., Hatton, T. A., Laibinis, P. E., *Langmuir*, 2000, 16(25), 9907. The presence of an organic phase can alter both the mass-transfer coefficient and the interfacial area, wherein the interfacial area is enhanced by means of bonding a thin organic, preferably hydrocarbon or polymeric layer, to fine, solid, magnetic nanoparticles. The coated magnetic particles are now capable of solubilizing gases, such as oxygen, and may be used in fermentation processes.

In general, absorption of sparingly soluble gases into a liquid is limited by the rate of mass transfer. This problem impacts, for example, the fields of catalysis (e.g., hydrogenation and oxygenation reactions), bioprocesses (e.g., oxygen transport in aerobic fermentations, oxygenation of blood), and toxic waste gas treatment. For example, in the field of bioprocesses, oxygen transfer poses a limitation to higher cell culture productivities. The use of a microdispersed organic phase into the fermentation broth with an enhanced capacity to solubilize oxygen has been found to alleviate oxygen limitations. M. Elibol, F. Mavituna, *Applied Microbiology and Biotechnology*, 1995, 43(2), 206; Rols, J., G. Goma, *Biotechnology Advances*, 1989. 7(1), p. 1–14; and Yamane, T., Yoshida, F., *Journal of Fermentation Technology*, 1974. 52(7), 445. Use of PFC-coated or hydrocarbon-coated nanoparticles instead of microdispersions, increases the efficiency of such dispersed phases by altering both the mass-transfer coefficient and the interfacial area available for mass transfer.

Methods of preparing fine magnetic particles coated with thin organic layers containing hydrocarbon groups capable of solubilizing gases are known in the art. U.S. Pat. No. 4,867,910 (Meguro, et al. Sep. 19, 1989) discloses ferrofluid compositions wherein an organic layer bearing hydrocarbon groups is bonded to magnetic particles. The organic layer can be selected from the group consisting of anionic surfactants having at least one polar group and wherein the anionic surfactant has at least 10 carbon atoms, and nonionic surfactants, e.g., an unsaturated fatty acid such as an oleic acid or a salt thereof, a petroleum sulfonate or the salt thereof, a synthetic sulfonate or a salt thereof, polybutene succinic acid or a salt thereof, a polybutene sulfonic acid or a salt thereof, polyoxyethylene nonyl phenyl ether and the like. However, such ferrofluid compositions provide for magnetic particles that are only colloidally stable in organic solvents, and aggregate, precipitate, and sediment in aqueous media such as fermentation broths and the like. Similarly, U.S. Pat. No. 6,780,343 (Hata, et al. Aug. 24, 2004) disclose stably dispersed magnetic viscous fluid wherein a magnetic particle is dispersed in an organic medium by means of bonding of magnetic particle core to a surfactant with a hydrocarbon group of 1 to 22 carbon atoms, preferred examples of the above hydrocarbon group of 1 to 22 carbon atoms includes alkyl groups of 1 to 18 carbon atoms, aryl groups of 6 to 14 carbon atoms, and arylalkyl or alkylaryl groups of 7 to 22 carbon atoms. As the more preferred species, methyl, ethyl, n-butyl, octyl, dodecyl groups and the like were mentioned. Likewise, such magnetic compositions are unstable in aqueous media.

Fine magnetic particles containing hydrocarbon groups that are stable in aqueous media are also known in the art. For example, U.S. Pat. No. 4,094,804 (Shimoiizaka, Jun. 13, 1978) discloses method for preparing a water base magnetic fluid wherein magnetic fluid is provided by adding an unsaturated fatty acid with 18 carbon atoms or a salt thereof into a colloidal solution of a ferromagnetic oxide powder in water, subsequently adding an anionic surfactant with 8 to 30 carbon atoms, or a non-ionic surfactant with 8 to 20 carbon atoms. Each particle of the ferromagnetic powder in the fluid is coated with a monomolecular layer of the ionized unsaturated fatty acid and with the non-ionic or anionic surfactant layer being adsorbed on the first monomolecular layer. However, the adsorption of an non-ionic surfactant upon anionic surfactant or cationic surfactant upon anionic surfactant on the surface of the magnetic particles without chemical or covalent bonding of the surfactants inevitably leads to instability of the resulting doubly-coated magnetic particles. That is, the second coating layer dissociates and desorbs from the first coating layer in the presence of living microorganisms and cells, metal ions and the like ingredients of the fermentation broths, by mass action law. The components of the second coating layer desorbed and dissolved in said fermentation broths are toxic to the living microorganisms and cells and being surface active, cause excessive foaming harmful to the bioprocess.

Fine magnetic particles containing hydrocarbon groups that are stable in aqueous media and wherein the first and second hydrocarbon layers are chemically bonded to each other so that the particles do not release surfactants in water are also known in the art. For example, Shen at al. (Shen, L.; Stachowiak, A.; Hatton, T. A.; Laibinis, P. E.; *Langmuir*, 2000, 16(25), 9907) discloses magnetic fluids consisting of magnetite nanoparticles and a surrounding bilayer of a primary and a secondary fatty acid surfactant comprising either 10-undecenoic acid or undecanoic acid for one or both of the surrounding layers. The olefin units capable of solubilizing gases were included within the structure as sites for polymerizing the shell components and increasing the stability of the magnetic fluid. Such particles do not release surfactant in aqueous milieu. However, we discovered that due to the unfavorable ionization pattern of the carboxylic groups exposed to the surface of the second olefinic layer, which are responsible for the colloidal stability of the particles, said particles must be exposed to pH above 7.4 and an aqueous medium devoid of significant content of metal ions to remain colloidally stable. Hence, said magnetite nanoparticles stabilized by polymerized fatty acids are disadvantageous in applications involving bioprocesses carried at pH 7.0 and below as well as in the presence of metal ions such as calcium, magnesium, and the like.

Polymer-stabilized magnetic particles, due to their relatively rapid magnetic separation, have been used in biomedical and bioengineering, such as cell separation, immunoassay, and nucleic acids concentration. Y. Haik, V. Pai, C. J., *Che J. Magn. Magn. Mater.*, 1999, 194, 254; K. Sugibayashi, Y. Morimoto, T. Nadai, Y. Kato, *Chem. Pharm. Bull*, 1977, 25, 3433; M. Mary In: U. Hafeli, W. Schutt and M. Zborowski, Editors, Scientific and Clinical Applications of Magnetic Carriers, Plenum Press, New York (1997), p. 303.; A. Elaissari, M. Rodrigue, F. Meunier, C. Herve, *J. Magn. Magn. Mater.*, 2001, 225, 127. In addition, magnetic polymeric particles offer a high potential in several areas of application, such as detoxification of biological fluids and the magnetic guidance of particle systems for specific drug delivery processes. P. K. Gupta, C. T. Hung, *Life Sci.*, 1989, 44, 175. The hydrophilic magnetic latexes have been reported by Kawaguchi et al. by using acrylamide as the principal monomer. H. Kawaguchi, K. Fujimoto, Y. Nakazawa, M. Sakagawsa, Y. Ariyoshi, M. Shidara, H. Okazaki, Y. Ebisawa, *Colloid Surf. A*, 1996, 109, 147. Another type of hydrophilic magnetic particles has been reported by Sauzedde et al. using a particle-coagulation methodology. F. Sauzedde, A. Elaissari, C. Pichot, *Colloid Polym. Sci.*, 1999, 277, 846; F. Sauzedde, A. Elaissari, C. Pichot, *Colloid Polym. Sci.*, 1999, 277, 1041; K. Furusawa, K. Nagashima, C. Anzai, *Colloid Polym. Sci.*, 1994, 272, 1104. Hydrophilic thermally sensitive latexes have been obtained by encapsulating adsorbed iron oxide nanoparticles onto oppositely charged polystyrene-core/poly(N-isopropylacrylamide)-shell. The encapsulation has been performed using water-soluble monomers only (N-isopropylacrylamide, N-N'methylene bis-acrylamide and itaconic acid). The final particles exhibit thermal-sensitive property. In addition, various original methods (via non-conventional polymerization) have been investigated using natural polymers or proteins. However, the aforementioned methods in the elaboration of magnetic polymeric latexes lead to submicron particles size (generally above 500 nm) with appreciable iron oxide content.

However, none of the aforementioned research utilized fluorine-containing polymers for the stabilization of magnetic particles. Notwithstanding the fact that fluorinated polymers have a range of remarkable properties including exceptional chemical and biological inertness, and a high oxygen-dissolving capacity. These fluorinated polymers are advantageously used as oxygen carriers in applications such as blood substitutes for oxygen delivery in different clinical settings, as well as for enhancement of bioproduction. R. E. Banks, B. E. Smart, J. C. Tatlow Organofluorine Chemistry, Principles and Commercial Applications, Plenum Press, New York (1994); S. F. Flaim, *Biotech.*, 1994, 22, 1043; M. P. Krafft, J. G. Riess, J. G. Weers, The design and engineering of oxygen-delivering fluorocarbon emulsions. In: S. Benita, Editor, Submicronic Emulsions in Drug Targeting and Delivery, Harwood Academic Publ., Amsterdam (1998), pp. 235–333; G. Riess, M. Le Blanc, *Angew. Chem. Int. Ed. Engl.*, 1978, 17, 621; Dixon, D D, Holland, D G., Fluorocarbons: properties and syntheses, Federation Proceedings, Volume 34, Issue 6, May 1975, Pages 1444–1448; McMillan, J. D., Wang, D. I., *Ann NY Acad Sci.*, 1990, 589:283–300.

U.S. Pat. No. 5,695,901 relates to a method for producing nano-size magnetic iron oxide particles. An iron reactant is contained in a disperse phase, reacted with a basic reactant and subjected to a controlled oxidation by the addition of an oxygen-containing oxidant. Precursor particles are precipitated in droplets of a disperse aqueous phase of the microemulsion. The precursor particles are oxidized in a carefully controlled environment to form the desired magnetic particles and to avoid overoxidation to produce undesirable nonmagnetic particles, such as hematite. However, the presence of oxygen-dissolving fluoropolymers would make such controlled oxidations difficult if not impossible.

U.S. Pat. No. 5,725,802 relates to a process for the preparation of metal oxide particles including magnetic iron oxide particles. Water-in-oil microemulsions are formed in which the oil used is Galden HT70 (a fluorinated oil with high vapour pressure) and the like, and metal ions in the aqueous phase are reacted with a gaseous or vapor reactant. The resulting nanoparticles are coated with perfluoroether, such as phosphoric monoester having perfluoropolyether hydrophobic chain and average MW of approximately 3000 and the like, and are hydrophobic and water-insoluble. Such hydrophobicity and difficulty of separation of the coated nanoparticles from the fluorinated oil emulsion present a hurdle in using the particles in aqueous-based, biological milieu.

U.S. Pat. No. 5,670,088 relates to a method for forming mixed metal oxide particles. A microemulsions is used which includes a perfluoropolyether oil and a perfluoropolyether surfactant. The method further involves mixing one metal in an aqueous phase with a second metal in a perfluoropolyether oil phase. The addition of an alkali solution is accompanied by heating to form the desired oxide. The coated nanoparticles are hydrophobic.

In industrial fermentation technology, the rate of oxygen supply to submerged cultures has often been identified as a limiting factor. This occurs when the oxygen transfer rate from sparged air is less than the cellular oxygen consumption rate, resulting in dissolved oxygen levels below the critical concentration needed to maintain metabolic activity. In conventionally aerated bioreactors, low oxygen solubility (0.28 mmol/dm$^3$ at 20° C.) combined with slow oxygen transfer rates often led to inhibition of growth and have other negative effects on cells.

The absorption rate of oxygen into liquid media used in bioprocesses such as fermentation processes and the like in the presence of a second, dispersed, organic phase can be significantly increased, because of the higher solubility and diffusivity of oxygen in the organic phase. Cho, M. H. and Wang, S. S., *Biotechnol. Lett.,* 1988, 10, 855; Hassan, I. T. M. and Robinson, C. W., 1977, *Biotechnol. Bioengng,* 1977, 19, 661; Ho, C. S., Ju, L.-K. and Baddour, R. F., *Biotechnol. Bioengng,* 1990, 36, 1110; Ju, L.-K., Lee, J. F. and Armiger, W. B., *Biotechnol. Prog.,* 1991, 7, 323; Junker, B. H., Wang, D. I. C. and Hatton, T. A., *Biotechnol. Bioengng,* 1990, 35, 586. The use of an organic phase in a fermentation broth can cause some negative effects on the cell growth and productivity. Nagy, E., *Advances in Biochemical Engineering/Biotechnology,* 2002, 75, 51. After prolonged contact, the culture system can become unstable due to loss of activity of the microbial cells, toxicity of the oxygen carriers, and/or the increased cell adsorption at the water/oil interface. Chandler, D., Davey, M. R., Lowe, K. C. & Mulligan, B. J., *Biotechnol. Letters,* 1987, 9, 195; Lowe, K. C., King, A. T. & Mulligan, B. J., *Biotechnol.,* 1989, 7, 1037; Wang, D. I. C., Junker, B. H. & Hatton, T. A., *Biotechnol. Bioeng.,* 1990, 35, 578–585. Covalent attachment of the ultrathin, oxygen-permeable organic layers onto small particles advantageously eliminates direct mixing of the organic liquids with the cells; thus, the toxicity problems related to direct mixing can be avoided.

Without being bound by any theory, the presence of fine solid particles or liquid drops with large oxygen capacity is known in the art to alter the concentration gradient in the liquid boundary layer at the gas-liquid interface and, hence, the gas absorption rate. Alper, E.; Deckwer, W. D., *Chem. Eng. Sci.,* 1981, 36, 1097; Holstvoogd, R. D.; van Swaaij, W. P. M.; van Dierendonck, L. L., *Chem. Eng. Sci.,* 1988, 43, 2181; Demmink J. P.; Mehra, A.; Beenackers, A. A. C. M. *Chem. Eng Sci.,* 1998, 53, 2885; Bruining, W. J.; Joosten, G. E. H.; Beenackers, A. A. C. M.; Hofman, H., *Chem. Eng. Sci.,* 1986, 41, 1873; Rols, J. L.; Condoret, J. S.; Fonade, C.; Goma, G. *Biotechnol. Bioeng.,* 1990, 35, 427; Junker, B. H.; Hatton, T. A.; Wang, D. I. C. *Biotechnol. Bioeng.,* 1990, 35, 578; Junker, B. H.; Wang, D. I. C.; Hatton, T. A. *Biotechnol. Bioeng.,* 1990, 35, 586; Van Ede, C. J.; van Houten, R.; Beenackers, A. A. C. M., *Chem. Eng. Sci.,* 1995, 50, 2911; Chaudhari, R. V.; Jayasree, P.; Gupte, S. P.; Delmas, H., Chem. Eng. Sci., 1997, 52, 4197; Beenackers, A. A. C. M.; Van Swaaij, W. P. M., Chem. Eng. Sci., 1993, 48, 3109.

SUMMARY OF THE INVENTION

One aspect of the present invention relates to a nanoparticle comprising an inorganic compound associated with an organic phase, wherein the organic phase is capable of reversibly solubilizing a gas. In certain embodiments, the present invention relates to the aforementioned nanoparticle, wherein the inorganic compound is an inorganic oxide. In certain embodiments, the present invention relates to the aforementioned nanoparticle, wherein the inorganic compound is a transition metal oxide. In certain embodiments, the present invention relates to the aforementioned nanoparticle, wherein the inorganic compound is a Group 8–10 transition metal oxide. In certain embodiments, the present invention relates to the aforementioned nanoparticle, wherein the inorganic compound is a Group 8 transition metal oxide. In certain embodiments, the present invention relates to the aforementioned nanoparticle, wherein the inorganic compound is an iron oxide. In certain embodiments, the present invention relates to the aforementioned nanoparticle, wherein the inorganic compound is $Fe_2O_3$ or $Fe_3O_4$. In certain embodiments, the present invention relates to the aforementioned nanoparticle, wherein the inorganic compound is $Fe_3O_4$. In certain embodiments, the present invention relates to the aforementioned nanoparticle, wherein the nanoparticle is magnetic. In certain embodiments, the present invention relates to the aforementioned nanoparticle, wherein the nanoparticle is non-toxic. In certain embodiments, the present invention relates to the aforementioned nanoparticle, wherein the gas is oxygen. In certain embodiments, the present invention relates to the aforementioned nanoparticle, wherein the gas is $CO_2$. In certain embodiments, the present invention relates to the aforementioned nanoparticle, wherein the inorganic compound is incorporated within the interstices of a fluorine-containing polymer. In certain embodiments, the present invention relates to the aforementioned nanoparticle, wherein the fluorine-containing polymer is a copolymer. In certain embodiments, the present invention relates to the aforementioned nanoparticle, wherein the fluorine-containing polymer is a copolymer comprising a fluorinated moiety and a non-fluorinated moiety. In certain embodiments, the present invention relates to the aforementioned nanoparticle, wherein the gas is oxygen and the fluorine-containing polymer is capable of reversibly binding oxygen in an aqueous medium. In certain embodiments, the present invention relates to the aforementioned nanoparticle, wherein the gas is $CO_2$ and the fluorine-containing polymer is capable of reversibly binding $CO_2$ in an aqueous medium. In certain embodiments, the present invention relates to the aforementioned nanoparticle, wherein the organic phase comprises a first and second hydrocarbon layer chemically bonded to each other. In certain embodiments, the present invention relates to the aforementioned nanoparticle, wherein the first hydrocarbon layer comprises a carbonyl functional group. In certain embodiments, the present invention relates to the aforementioned nanoparticle, wherein the first hydrocarbon layer comprises a fatty acid. In certain embodiments, the present invention relates to the aforementioned nanoparticle, wherein the first hydrocarbon layer comprises oleic acid. In certain embodiments, the present invention relates to the aforementioned nanoparticle, wherein the second hydrocarbon layer comprises a hydrophilic group. In certain embodiments, the present invention relates to the aforementioned nanoparticle, wherein the second hydrocarbon layer comprises a nonionic and an anionic hydrophilic group. In certain embodiments, the present invention relates to the aforementioned nanoparticle, wherein the second hydrocarbon layer comprises a polyoxyalkylene sulfonate moiety. In certain embodiments, the present invention relates to the aforementioned nanoparticle, wherein the second hydrocarbon layer comprises a polyoxyethylene sulfonate moiety. In certain embodiments, the present invention relates to the aforementioned nanoparticle, wherein the first and second hydrocarbon layer are bonded together through a carbon-carbon single bond. In certain embodiments, the present invention relates to the aforementioned nanoparticle, wherein the gas is oxygen and the organic phase is capable of reversibly binding oxygen in an aqueous medium. In certain embodiments, the present invention relates to the aforementioned nanoparticle, wherein the nanoparticle is capable of forming an aqueous colloid. In certain embodiments, the present invention relates to the aforementioned nanoparticle, wherein the nanoparticle has a diameter of about 1 to about 1,000 nm. In certain embodiments, the present invention relates to the aforementioned nanoparticle, wherein the nanoparticle has a diameter of about 10 to about 100 nm. In certain embodiments, the present invention relates to the aforementioned nanoparticle, wherein the gas is oxygen. In certain embodiments, the present invention relates to the aforementioned nanoparticle, wherein the gas is $CO_2$.

In certain embodiments, the present invention relates to a composition, comprising any of the aforementioned embodiments of the nanoparticle. In certain embodiments, the composition is an aqueous colloid.

Another aspect of the invention relates to a method of preparing nanoparticles comprising an inorganic compound incorporated within the interstices of a fluorine-containing polymer comprising: (a) co-precipitating an inorganic salt in an aqueous solution in the presence of a fluorine-containing polymer; and (b) sonicating the mixture from step a), and isolating the nanoparticles. In certain embodiments, the present invention relates to the aforementioned method, wherein the aqueous solution is deaerated with an inert gas. In certain embodiments, the present invention relates to the aforementioned method, wherein the aqueous solution is deaerated with $N_2$ gas. In certain embodiments, the present invention relates to the aforementioned method, wherein the inorganic salt is a transition metal salt. In certain embodiments, the present invention relates to the aforementioned method, wherein the inorganic salt is a Group 8–10 transition metal salt. In certain embodiments, the present invention relates to the aforementioned method, wherein the inorganic salt is a Group 8 transition metal salt. In certain embodiments, the present invention relates to the aforementioned method, wherein the inorganic salt is an iron salt. In certain embodiments, the present invention relates to the aforementioned method, wherein the inorganic salt is a chloride salt. In certain embodiments, the present invention relates to the aforementioned method, wherein the inorganic salt is an iron-chloride salt. In certain embodiments, the present invention relates to the aforementioned method, wherein the inorganic salt comprises a mixture of Fe(II) and Fe(III) chloride salts. In certain embodiments, the present invention relates to the aforementioned method, wherein the aqueous solution of an inorganic salt is heated to about 65° C. to about 85° C. In certain embodiments, the present invention relates to the aforementioned method, wherein the aqueous solution of an inorganic salt is heated to about 70° C. to about 85° C. In certain embodiments, the present invention relates to the aforementioned method, wherein the aqueous solution of an inorganic salt is heated to about 75° C. to about 85° C. In certain embodiments, the present invention relates to the aforementioned method, wherein the aqueous solution of an inorganic salt is heated to about 80° C.

Another aspect of the present invention relates to a method of preparing nanoparticles comprising an inorganic compound associated with a hydrocarbon bilayer comprising a first hydrocarbon layer chemically bonded to a second hydrocarbon layer comprising: (a) coprecipitating an inorganic salt in an aqueous solution in the presence of a first hydrocarbon moiety capable of bonding with the inorganic compound, and (b) reacting the product from step a) with a second hyrocarbon moiety comprising a hydrophilic group, wherein the first hydrocarbon moiety chemically bonds to the second hyrdocarbon moiety to form the hydrocarbon bilayer. In certain embodiments, the present invention relates to the aforementioned method, wherein the aqueous solution is deaerated with an inert gas. In certain embodiments, the present invention relates to the aforementioned method, wherein the aqueous solution is deaerated with $N_2$ gas. In certain embodiments, the present invention relates to the aforementioned method, wherein the inorganic salt is a transition metal salt. In certain embodiments, the present invention relates to the aforementioned method, wherein the inorganic salt is a Group 8–10 transition metal salt. In certain embodiments, the present invention relates to the aforementioned method, wherein the inorganic salt is a Group 8 transition metal salt. In certain embodiments, the present invention relates to the aforementioned method, wherein the inorganic salt is an iron salt. In certain embodiments, the present invention relates to the aforementioned method, wherein the inorganic salt is a chloride salt. In certain embodiments, the present invention relates to the aforementioned method, wherein the inorganic salt is an iron-chloride salt. In certain embodiments, the present invention relates to the aforementioned method, wherein the inorganic salt comprises a mixture of Fe(II) and Fe(III) chloride salts. In certain embodiments, the present invention relates to the aforementioned method, wherein the first hydrocarbon moiety comprises a carbonyl functional group. In certain embodiments, the present invention relates to the aforementioned method, wherein the first hydrocarbon moiety comprises a fatty acid. In certain embodiments, the present invention relates to the aforementioned method, wherein the first hydrocarbon moiety comprises oleic acid. In certain embodiments, the present invention relates to the aforementioned method, wherein the second hydrocarbon moiety comprises a hydrophilic group. In certain embodiments, the present invention relates to the aforementioned method, wherein the hydrophilic group comprises a nonionic and an anionic group. In certain embodiments, the present invention relates to the aforementioned method, wherein the hydrophilic group comprises a polyoxyalkylene sulfonate. In certain embodiments, the present invention relates to the aforementioned method, wherein the hydrophilic group comprises a polyoxyethylene sulfonate moiety. In certain embodiments, the present invention relates to the aforementioned method, wherein the first and second hydrocarbon moieties are bonded together through a carbon-carbon single bond. In certain embodiments, the present invention relates to the aforementioned method, wherein the aqueous solution of an inorganic salt is heated to about 65° C. to about 85° C. In certain embodiments, the present invention relates to the aforementioned method, wherein the aqueous solution of an inorganic salt is heated to about 70° C. to about 85° C. In certain embodiments, the present invention relates to the aforementioned method, wherein the aqueous solution of an inorganic salt is heated to about 75° C. to about 85° C. In certain embodiments, the present invention relates to the aforementioned method, wherein the aqueous solution of an inorganic salt is heated to about 80° C.

Another aspect of the present invention relates to a method of increasing the amount of gas transfer to a medium comprising introducing to the medium nanoparticles comprising an inorganic compound associated with an organic phase, wherein the organic phase is capable of reversibly solubilizing a gas. In certain embodiments, the present invention relates to the aforementioned method, wherein the inorganic compound is a transition metal oxide. In certain embodiments, the present invention relates to the aforementioned method, wherein the inorganic compound is a Group 8–10 transition metal oxide. In certain embodiments, the present invention relates to the aforementioned method, wherein the inorganic compound is a Group 8 transition metal oxide. In certain embodiments, the present invention relates to the aforementioned method, wherein the inorganic compound is an iron oxide. In certain embodiments, the present invention relates to the aforementioned method, wherein the inorganic compound is $Fe_2O_3$ or $Fe_3O_4$. In certain embodiments, the present invention relates to the aforementioned method, wherein the inorganic compound is $Fe_3O_4$. In certain embodiments, the present invention relates to the aforementioned method, wherein the gas transfer is increased by greater than about 400%. In certain embodiments, the present invention relates to the aforementioned method, wherein the nanoparticles are magnetic. In certain embodiments, the present invention relates to the aforementioned method, wherein the gas is oxygen. In certain embodiments, the present invention relates to the aforementioned method, wherein the gas is $CO_2$. In certain embodiments, the present invention relates to the aforementioned method, wherein the inorganic compound is incorporated within the interstices of a fluorine-containing polymer. In certain embodiments, the present invention relates to the aforementioned method, wherein the fluorine-containing polymer is a copolymer. In certain embodiments, the present invention relates to the aforementioned method, wherein the fluorine-containing polymer is a copolymer comprising a fluorinated moiety and a non-fluorinated moiety. In certain embodiments, the present invention relates to the aforementioned method, wherein the fluorine-containing polymer is capable of reversibly binding the gas in an aqueous medium. In certain embodiments, the present invention relates to the aforementioned method, wherein the organic phase comprises a first and second hydrocarbon layer chemically bonded to each other. In certain embodiments, the present invention relates to the aforementioned method, wherein the first hydrocarbon layer comprises a carbonyl functional group. In certain embodiments, the present invention relates to the aforementioned method, wherein the first hydrocarbon layer comprises a fatty acid. In certain embodiments, the present invention relates to the aforementioned method, wherein the first hydrocarbon layer comprises oleic acid. In certain embodiments, the present invention relates to the aforementioned method, wherein the second hydrocarbon layer comprises a hydrophilic group. In certain embodiments, the present invention relates to the aforementioned method, wherein the hydrophilic group comprises a non-ionic and anionic group. In certain embodiments, the present invention relates to the aforementioned method, wherein the hydrophilic group comprises a polyoxyalkylene sulfonate moiety. In certain embodiments, the present invention relates to the aforementioned method, wherein the hydrophilic group comprises a polyoxyethylene sulfonate moiety. In certain embodiments, the present invention relates to the aforementioned method, wherein the first and second hydrocarbon layer are bonded together through a carbon-carbon single bond. In certain embodiments, the present invention relates to the aforementioned method, wherein the gas is oxygen. In certain embodiments, the present invention relates to the aforementioned method, wherein the gas is $CO_2$. In certain embodiments, the present invention relates to the aforementioned method, wherein the nanoparticles are separated from the medium by exposing the medium to magnetic fields and transferring the medium elsewhere.

Another aspect of the present invention relates to a method of enhancing cell growth in fermentation processes comprising introducing to a fermentation medium comprising a cell culture nanoparticles comprising an inorganic compound associated with an organic phase, wherein the organic phase is capable of reversibly solubilizing oxygen, thereby increasing the amount of oxygen transfer to the fermentation medium. In certain embodiments, the present invention relates to the aforementioned method, wherein the inorganic compound is a transition metal oxide. In certain embodiments, the present invention relates to the aforementioned method, wherein the inorganic compound is a Group 8–10 transition metal oxide. In certain embodiments, the present invention relates to the aforementioned method, wherein the inorganic compound is a Group 8 transition metal oxide. In certain embodiments, the present invention relates to the aforementioned method, wherein the inorganic compound is an iron oxide. In certain embodiments, the present invention relates to the aforementioned method, wherein the inorganic compound is $Fe_2O_3$ or $Fe_3O_4$. In certain embodiments, the present invention relates to the aforementioned method, wherein the inorganic compound is $Fe_3O_4$. In certain embodiments, the present invention relates to the aforementioned method, wherein the oxygen transfer is increased by greater than about 400%. In certain embodiments, the present invention relates to the aforementioned method, wherein the nanoparticles are magnetic. In certain embodiments, the present invention relates to the aforementioned method, wherein the inorganic compound is incorporated within the interstices of a fluorine-containing polymer. In certain embodiments, the present invention relates to the aforementioned method, wherein the fluorine-containing polymer is a copolymer. In certain embodiments, the present invention relates to the aforementioned method, wherein the fluorine-containing polymer is a copolymer comprising a fluorinated moiety and a non-fluorinated moiety. In certain embodiments, the present invention relates to the aforementioned method, wherein the fluorine-containing polymer is capable of reversibly binding oxygen in an aqueous medium. In certain embodiments, the present invention relates to the aforementioned method, wherein the organic phase comprises a first and second hydrocarbon layer chemically bonded to each other. In certain embodiments, the present invention relates to the aforementioned method, wherein the first hydrocarbon layer comprises a carbonyl functional group. In certain embodiments, the present invention relates to the aforementioned method, wherein the first hydrocarbon layer comprises a fatty acid. In certain embodiments, the present invention relates to the aforementioned method, wherein the first hydrocarbon layer comprises oleic acid. In certain embodiments, the present invention relates to the aforementioned method, wherein the second hydrocarbon layer comprises a hydrophilic group. In certain embodiments, the present invention relates to the aforementioned method, wherein the hydrophilic group comprises a non-ionic and anionic group. In certain embodiments, the present invention relates to the aforementioned method, wherein the hydrophilic group comprises a polyoxyalkylene sulfate moiety. In certain embodiments, the present invention relates to the aforementioned method, wherein the hydrophilic group comprises a polyoxyethylene sulfate moiety. In certain embodiments, the present invention relates to the aforementioned method, wherein the first and second hydrocarbon layer are bonded together through a carbon-carbon single bond. In certain embodiments, the present invention relates to the aforementioned method, wherein the nanoparticles are separated from the fermentation medium by exposing the fermentation medium to magnetic fields and transferring the fermentation medium elsewhere.

These embodiments of the present invention, other embodiments, and their features and characteristics, will be apparent from the description, drawings and claims that follow.

DETAILED DESCRIPTION OF THE INVENTION

Overview

Figure 1:
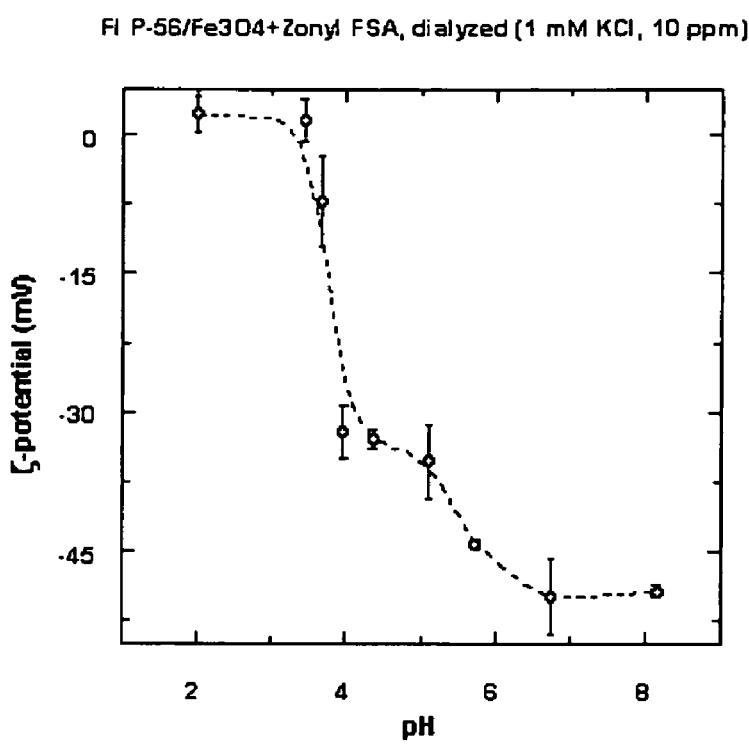
FIG. 1 depicts the ζ-potential and weight-average diameter of magnetic nanoparticles modified by fluoropolymers as a function of pH as described in Example 1.
Figure 1:
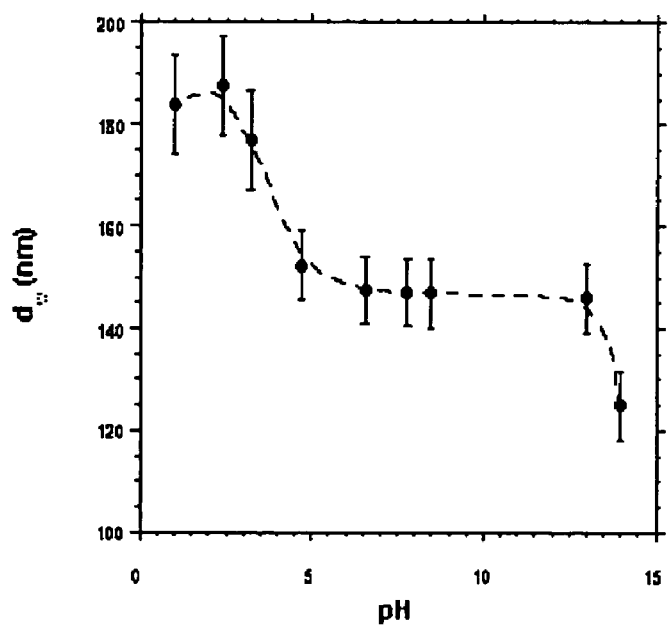

In part the present invention relates to inorganic compounds associated with an organic phase that are stable in aqueous media and provide enhanced oxygen delivery useful in such processes as fermentation. The organic phase may be a fluoropolymer capable of reversibly binding a gas. The organic phase may also be a hydrocarbon bilayer, comprising a first and second hydrocarbon layer chemically bonded together, and wherein the bilayer is capable of reversibly binding a gas. The particles remain colloidally stable under any practical pH range and in the presence of metal ions.

In another embodiment, the present invention relates to a composition comprising a nanoparticle of the present invention. In a further embodiment, the composition is an aqueous colloid.

The compositions of the present invention may further include suitable inorganic salts, glucose, and other excipients commonly used in the art of fermentation. The surface modification aspect allows the compatibility between the particles and fluid to be controllably adjusted to achieve a non-toxic and useful enhancement of the solubility of oxygen and optionally other gases. The modified magnetic nanoparticles are well-suited for easy magnetic recovery from and recycling in a fermentation broth. The coated nanoparticles are further characterized by favorable nanometer size and surface-to-volume ratio making them advantageous in separation processes.

Manufacture of the magnetic particles of the present invention may be accomplished by scalable processes of precipitation of inorganic salts. In another embodiment, the present invention relates to a method of preparing nanoparticles comprising an inorganic compound incorporated within the interstices of a fluorine-containing polymer comprising: a) co-precipitating an inorganic salt in an aqueous solution in the presence of a fluorine-containing polymer; and b) sonicating the mixture from step a), and isolating the nanoparticles.

In another embodiment, the present invention relates to a method of preparing nanoparticles comprising an inorganic compound associated with a hydrocarbon bilayer comprising a first hydrocarbon layer chemically bonded to a second hydrocarbon layer comprising: a) coprecipitating an inorganic salt in an aqueous solution in the presence of a first hydrocarbon moiety capable of bonding with the inorganic compound, and b) reacting the product from step a) with a second hyrocarbon moiety comprising a hydrophilic group, wherein the first hydrocarbon moiety chemically bonds to the second hyrdocarbon moiety to form the hydrocarbon bilayer.

In another embodiment, the present invention relates to a method of increasing the amount of gas transfer to a medium comprising introducing to the medium nanoparticles comprising an inorganic compound associated with an organic phase, wherein the organic phase is capable of reversibly solubilizing a gas. In a further embodiment, the organic phase is a fluoropolymer. In a further embodiment, the organic phase is a hydrocarbon bilayer comprising a first hydrocarbon moiety and a second hydrocarbon moiety chemically bonded to each other.

In another embodiment, the present invention relates to a method of enhancing cell growth in fermentation processes, comprising introducing to a fermentation medium comprising a cell culture nanoparticles comprising an inorganic compound associated with an organic phase, thereby increasing the amount of oxygen transfer to the fermentation medium. In a further embodiment, the organic phase is a fluoropolymer. In a further embodiment, the organic phase is a hydrocarbon bilayer comprising a first hydrocarbon moiety and a second hydrocarbon moiety chemically bonded to each other.

By virtue of the methods of the present invention, the solubility of the gas in the mixture is increased because the solubility in the organic phase is greater than the solubility of the gas in water. For example, oxygen solubility in PFCs can be 12 to 16 times larger than in water, and 4 to 7 times larger in hydrocarbons than in water. Moreover, because gas solubilization is generally a reversible process, the nanoparticles can either get loaded with gas from the medium or they can unload the gas to the medium, depending on the surrounding concentration gradient.

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The term "associated with" as used herein in such phrases as, for example, "an inorganic compound associated with an organic phase," refers to the presence of either weak or strong or both interactions between molecules. For example weak interactions may include, for example, electrostatic, van der Waals, or hydrogen-bonding interactions. Stronger interactions, also referred to as being chemically bonded, refer to, for example, covalent, ionic, or coordinative bonds between two molecules. The term "associated with" also refers to a compound that may be physically intertwined within the foldings of another molecule, even when none of the above types of bonds are present. For example, an inorganic compound may be considered as being in association with a fluoropolymer by virtue of it existing within the interstices of the fluoropolymer.

The terms "comprise" and "comprising" are used in the inclusive, open sense, meaning that additional elements may be included.

The term "including" is used to mean "including but not limited to". "Including" and "including but not limited to" are used interchangeably.

The term "polymer" is used to mean a large molecule formed by the union of repeating units (monomers). The term polymer also encompasses copolymers.

The term "copolymer" is used to mean a polymer of two or more different monomers.

The term "fluorocarbon" as used herein means a halocarbon compound in which fluorine replaces some or all hydrogen atoms.

The term "fluorine-containing polymer" also referred to as "fluoropolymer" is used to mean a polymer comprising fluorine. Preferably, the flourine-containing polymer is used to mean a fluorocarbon containing polymer.

The terms "Lewis base" and "Lewis basic" are art-recognized and generally include a chemical moiety, a structural fragment or substituent capable of donating a pair of electrons under certain conditions. It may be possible to characterize a Lewis base as donating a single electron in certain complexes, depending on the identity of the Lewis base and the metal ion, but for most purposes, however, a Lewis base is best understood as a two electron donor. Examples of Lewis basic moieties include uncharged compounds such as alcohols, thiols, and amines, and charged moieties such as alkoxides, thiolates, carbanions, and a variety of other organic anions. A Lewis base, when coordinated to a metal ion, is often referred to as a ligand.

The terms "Lewis acid" and "Lewis acidic" are art-recognized and refer to chemical moieties which can accept a pair of electrons from a Lewis base as defined above.

The term "particle size" is used to mean a number- or weight-average particle size as measured by conventional particle size measuring techniques well known to those skilled in the art, such as, for example, dynamic or static light scattering, sedimentation field flow fractionation, photon correlation spectroscopy, or disk centrifugation. By "an effective average particle size of less than about 1000 nm" it is meant that at least about 90% of the particles have a weight average particle size of less than about 1000 nm when measured by the above-noted techniques.

The term "interstices" is used to mean a space, especially a small or narrow one, between things or parts.

The term "aliphatic" is an art-recognized term and includes linear, branched, and cyclic alkanes, alkenes, or alkynes. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$–$C_{30}$ for straight chain, $C_3$–$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to ten carbons, alternatively from one to about six carbon atoms in its backbone structure. Likewise, "lower alkenyl" and "lower alkynyl" have similar chain lengths.

The term "aralkyl" is art-recognized, and includes alkyl groups substituted with an aryl group (e.g., an aromatic or heteroaromatic group).

The terms "alkenyl" and "alkynyl" are art-recognized, and include unsaturated aliphatic groups analogous in length and possible substitution to the alkyls described above, but that contain at least one double or triple bond respectively.

The term "heteroatom" is art-recognized, and includes an atom of any element other than carbon or hydrogen. Illustrative heteroatoms include boron, nitrogen, oxygen, phosphorus, sulfur and selenium, and alternatively oxygen, nitrogen or sulfur.

The term "aryl" is art-recognized, and includes 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and apply to 1,2-, 1,3- and 1,4-disubstituted benzenes, respectively. For example, the names 1,2-dimethylbenzene and ortho-dimethylbenzene are synonymous.

The terms "heterocyclyl" and "heterocyclic group" are art-recognized, and include 3- to about 10-membered ring structures, such as 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" and "polycyclic group" are art-recognized, and include structures with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms, e.g., three or more atoms are common to both rings, are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle" is art recognized and includes an aromatic or non-aromatic ring in which each atom of the ring is carbon. The flowing art-recognized terms have the following meanings: "nitro" means —$NO_2$; the term "halogen" designates —F, —Cl, —Br or —I; the term "sulfhydryl" means —SH; the term "hydroxyl" means —OH; and the term "sulfonyl" means —$SO_2$.

The terms "amine" and "amino" are art-recognized and include both unsubstituted and substituted amines, e.g., a moiety that may be represented by the general formulas:

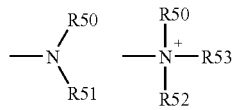

wherein R50, R51 and R52 each independently represent a hydrogen, an alkyl, an alkenyl, —$(CH_2)_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —$(CH_2)_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and includes a moiety that may be represented by the general formula:

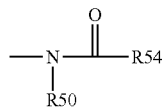

wherein R50 is as defined above, and R54 represents a hydrogen, an alkyl, an alkenyl or —$(CH_2)_m$—R61, where m and R61 are as defined above.

The term "amido" is art recognized as an amino-substituted carbonyl and includes a moiety that may be represented by the general formula:

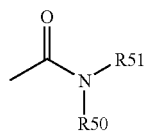

wherein R50 and R51 are as defined above. Certain embodiments of the amide in the present invention will not include imides which may be unstable.

The term "alkylthio" is art recognized and includes an alkyl group, as defined above, having a sulfur radical attached thereto. In certain embodiments, the "alkylthio" moiety is represented by one of —S-alkyl, —S-alkenyl, —S-alkynyl, and —S—$(CH_2)_m$—R61, wherein m and R61 are defined above. Representative alkylthio groups include methylthio, ethyl thio, and the like.

The term "carbonyl" is art recognized and includes such moieties as may be represented by the general formulas:

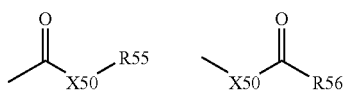

wherein X50 is a bond or represents an oxygen or a sulfur, and R55 represents a hydrogen, an alkyl, an alkenyl, —$(CH_2)_m$—R61 or a pharmaceutically acceptable salt, R56 represents a hydrogen, an alkyl, an alkenyl or —$(CH_2)_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiocarbonyl" group. Where X50 is a sulfur and R55 or R56 is not hydrogen, the formula represents a "thioester." Where X50 is a sulfur and R55 is hydrogen, the formula represents a "thiocarboxylic acid." Where X50 is a sulfur and R56 is hydrogen, the formula represents a "thioformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art recognized and include an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O—alkyl, —O—alkenyl, —O—alkynyl, —O—$(CH_2)_m$—R61, where m and R61 are described above.

The term "sulfonate" is art recognized and includes a moiety that may be represented by the general formula:

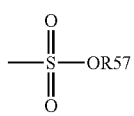

in which R57 is an electron pair, hydrogen, alkyl, cycloalkyl, or aryl.

The term "sulfate" is art recognized and includes a moiety that may be represented by the general formula:

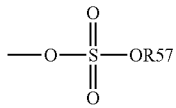

in which R57 is as defined above.

The term "sulfonamido" is art recognized and includes a moiety that may be represented by the general formula:

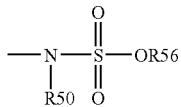

in which R50 and R56 are as defined above.

The term "sulfamoyl" is art-recognized and includes a moiety that may be represented by the general formula:

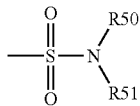

in which R50 and R51 are as defined above.

The term "sulfonyl" is art recognized and includes a moiety that may be represented by the general formula:

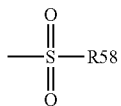

in which R58 is one of the following: hydrogen, alkyl, alkenyl, alkynyl, cycloalkyl, heterocyclyl, aryl or heteroaryl.

The term "sulfoxido" is art recognized and includes a moiety that may be represented by the general formula:

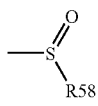

in which R58 is defined above.

The term "phosphoramidite" is art recognized and includes moieties represented by the general formulas:

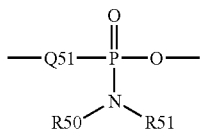 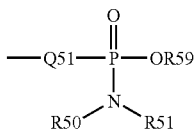

wherein Q51, R50, R51 and R59 are as defined above.

The term "phosphonamidite" is art recognized and includes moieties represented by the general formulas:

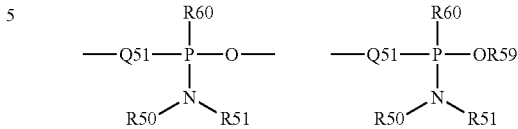

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, etc., when it occurs more than once in any structure, is intended to be independent of its definition elsewhere in the same structure unless otherwise indicated expressly or by the context.

For purposes of this invention, the chemical elements are identified in accordance with the Periodic Table of the Elements, CAS version, Handbook of Chemistry and Physics, 67th Ed., 1986–87, inside cover.

Inorganic Compound

The inorganic compound used to prepare the nanoparticles of the present invention can generally be any inorganic compound prepared in an aqueous medium. In another embodiment, the inorganic compound is a metal oxide prepared by dissolving a metal salt precursor in an aqueous medium. The metal may be in the form of a cation belonging to Groups 1–15 of the Periodic Table. These metals include, for example, Li, Na, K, Mg, Ca, Sr, Ba, Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, and Hg. The term "metal" is also used to include metalloids belonging to groups 13–15. These metalloids include B, Al, Ga, In, Tl, Si, Ge, Sn, Pb, As, Sb, and Bi. Preferably, the metal cations may belong to Groups 8–10 which include Fe, Ru, Os, Co, Rh, Ir, Ni, Pd, and Pt. Preferably, the metal oxides are magnetic metal oxides. The magnetic metal oxide may include Fe either as Fe(II), Fe(III), or a mixture of Fe(II)/Fe(III). Non-limiting examples of such oxides include FeO, $Fe_2O_3$, and $Fe_3O_4$. The inorganic compound may also be a mixed oxide of the type $M1_xM2_{3-x}O_4$, wherein M1 represents a divalent metal ion and M2 represents a trivalent metal ion. For example, the inorganic compound may be magnetic ferrites of the formula $M1Fe_2O_4$, wherein M1 represents a divalent ion selected from the following: Mn, Co, Ni, Cu, Zn, or Ba, pure or in admixture with each other or in admixture with ferrous ions.

Fluorine-Containing Polymer

The fluorine containing polymers used in the present invention may be any polymer or copolymer where at least one hydrogen atom has been replaced by a fluorine atom and is capable of forming a dispersion in aqueous $NH_4OH$. Such polymers include, for example, those fluorine containing polymers that comprise a repeating unit selected from the following: $(CF_2CF_2O)_n$, $(CF_2O)_n$, $(CF_2CF_2CF_2O)_n$, $(CF_2CF_2)_n$, $(CF_2CF_2CH_2O)$, $(CF(CF_3)CF_2O)_n$, $(CF(CF_3)O)_n$, or combinations thereof. These repeating units may be further substituted with groups designed to enhance dispersability in aqueous $NH_4OH$, or the polymer may be end capped with groups designed to enhance dispersability. In the case where the fluorine containing polymer is a copolymer, the repeating units may be distributed statistically or randomly throughout the copolymer. Also in the case of copolymers, the non-fluorinated moiety may be designed to increase dispersability in aqueous $NH_4OH$.

Common examples of fluoropolymers or fluorocopolymers include perfluoropolyethers, hexafluoropropylene oxide and hexafluoropropene oxide, hexafluoroproylene epoxide, hexafluoropropene epoxide, hexafluoropropylene, hexafluoropropene. Suitable fluoropolymers or fluorocopolymers are also available commercially under the tradenames FOMBLIN Y®, FOMBLIN Z®, and GALDEN®, all of Ausimont USA; KRYTOX®, ZONYL® FSA, and NAFION®, all of Dupont, and DYNEON™ of 3M.

Particle Characterization

The magnetic nanoparticles described in Example 1 were characterized for their size by dynamic light scattering setup (Brookhaven Instruments Co.) and for electrophoretic properties by the ZetaPals Zeta Potential Analyzer (Brookhaven Instruments Co.) with a built-in software that employs Smoluchowski ζ-potential model. The results are shown in FIG. 1. As is seen, the particles exhibit a weight-average diameter of about 150 nm and a negative surface charge in the pH range relevant for bioprocesses. The particles are thus charge-stabilized and can stay dispersed indefinitely.

The particle diameter of the nanoparticles is preferably 0.001 to 100 μm. If the particle diameter is less than about 10 nm, it will be difficult to gain the movement of said magnetic particles significantly on application of a magnetic field because of Brownian motion effects. If it exceeds 1000 nm, the magnetic particles tend to sediment in the dispersive medium, thus affecting the dispersion stability. The more preferred range is 10 to 100 nm.

Benign Nature of Fluoropolymer-Coated Magnetic Nanoparticles and Magnetic Fluids Comprising Them.

Figure 2:
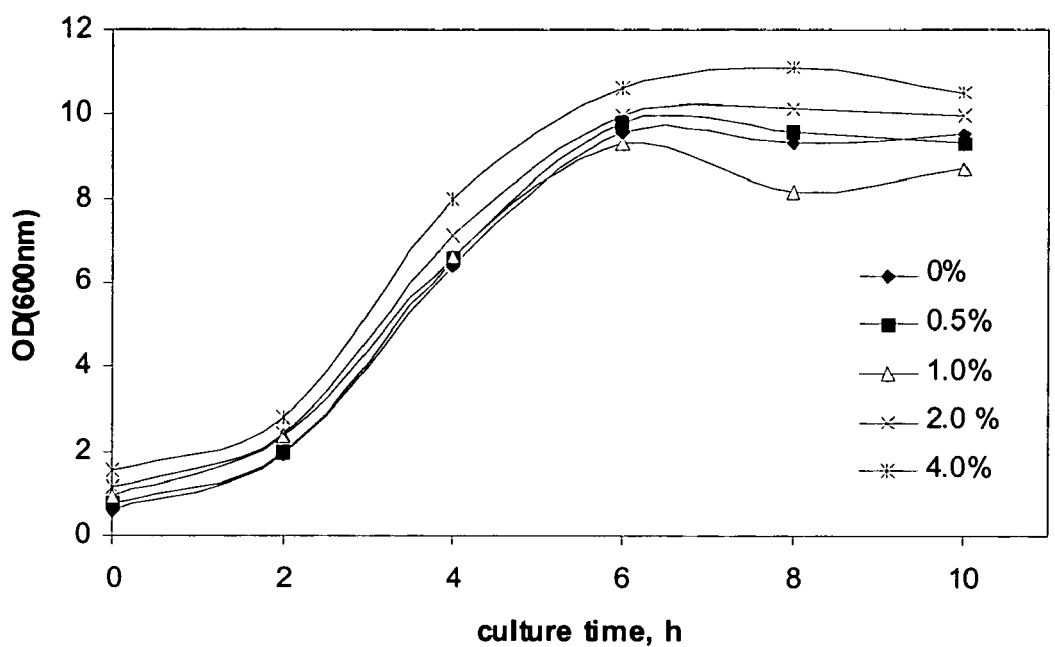
FIG. 2 depicts the results of the toxicity test of the fluoropolymer-modified magnetic nanoparticles synthesized as described in Example 1. The *E. coli* cell growth was monitored by measured optical density at 600 nm. The nanoparticle weight percent are as indicated.

$Fe_3O_4$ Nanoparticles Stabilized by Fluoropolymer having Weakly Acidic Charges The toxicity of nanoparticles synthesized with a pre-prepared fluoropolymer having weakly acidic charges (Fluorolink™), as described in Example 1, towards *E. coli* cells was tested in the shake-flask batch experiment described in Example 2. As is seen in FIG. 2, the fluoropolymer coated magnetic particles were found to be non-toxic and did not inhibit cell growth.

Figure 5:
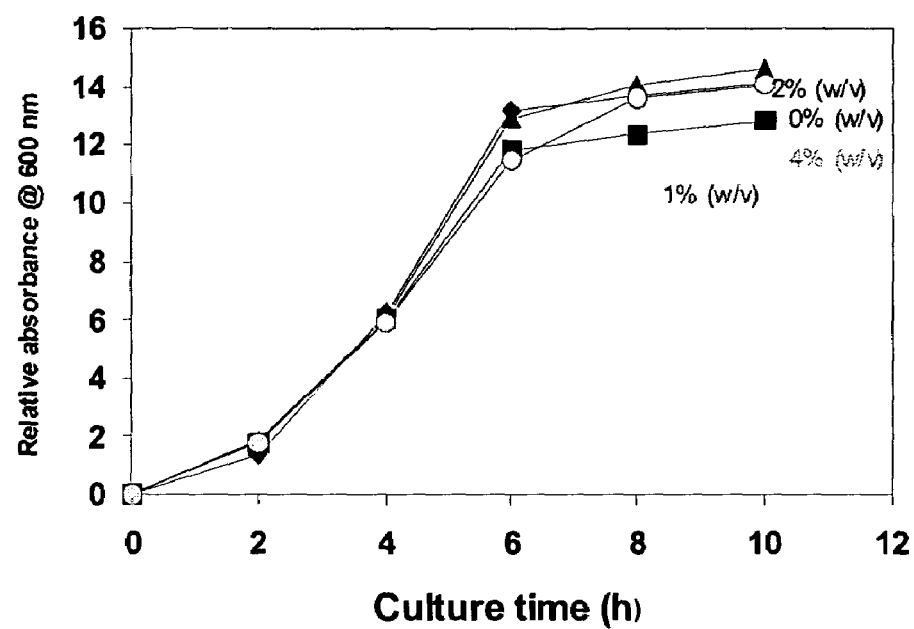
FIG. 5 depicts the results of the toxicity test of the fluoropolymer-modified magnetic nanoparticles synthesized as described in Example 7. The *E. coli* cell growth was monitored by measured optical density of the particle/cell suspension at 600 nm. The content of particles in volume percent is indicated.
Figure 6:
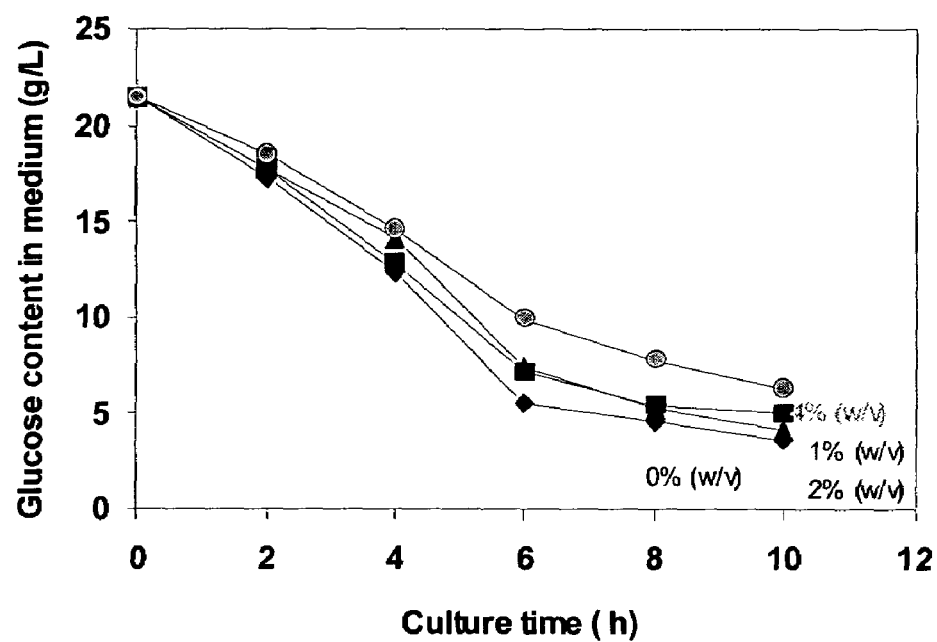
FIG. 6 depicts the results of the toxicity test of the fluoropolymer-modified magnetic nanoparticles synthesized as described in Example 7, in terms of glucose consumption, which is indicative of the cell growth and proliferation. The content of the particles in volume percents is indicated.

$Fe_3O_4$ Nanoparticles Stabilized by Fluoropolymer having Strongly Acidic Charges Nanoparticles were prepared using a fluoropolymer having strong acidic charges as described in Example 6. The particles were evaluated for their potential effects on the growth of bacterial cells. Toxicity of the particles to *E. coli* cells was tested in the shake-flask batch experiment. The test conditions were as described in Example 2. As is seen in FIGS. 5 and 6, the fluoropolymer-coated magnetic particles were found to be non-toxic and did not inhibit the cell growth. No foaming was observed in the cell/particle suspensions.

In a separate series of experiments, a weighed amount of magnetic particles was added to a weighed amount of the fermentation and culture seed broths and a shake-test experiment was conducted (for description of the broths and shake-test experiments, see Example 2). Then the 15-mL polypropylene vials containing cells and magnetic particles were subjected to separation using a Model L-1 Frantz Isodynamic Magnetic Separator (S. G. Frantz Co., Trenton, N.J.). When subjected to a powerful magnetic field, the fluoropolymer-coated particles rapidly sedimented to the bottom of the vial, leaving the suspended cells on top. The layers of the dark-brown particles and yellowish cell suspension were clearly distinguishable. The liquid layer containing suspended cells was gently removed by a pipette, and equal amount of deionized water was added. The suspension of particles was shaken and again subjected to separation by the magnetic field. The procedure of the liquid replacement, separation, and removal was repeated three times. Following repeated separation and washing, the magnetic particles were dried in the oven at 90° C. until constant weight and the final weight was compared to the initial particle content of the corresponding sample. Five samples were tested for the particles recovery, which was measured to be 99±5%. Hence, complete recovery of the magnetic particles was achieved.

Figure 4:
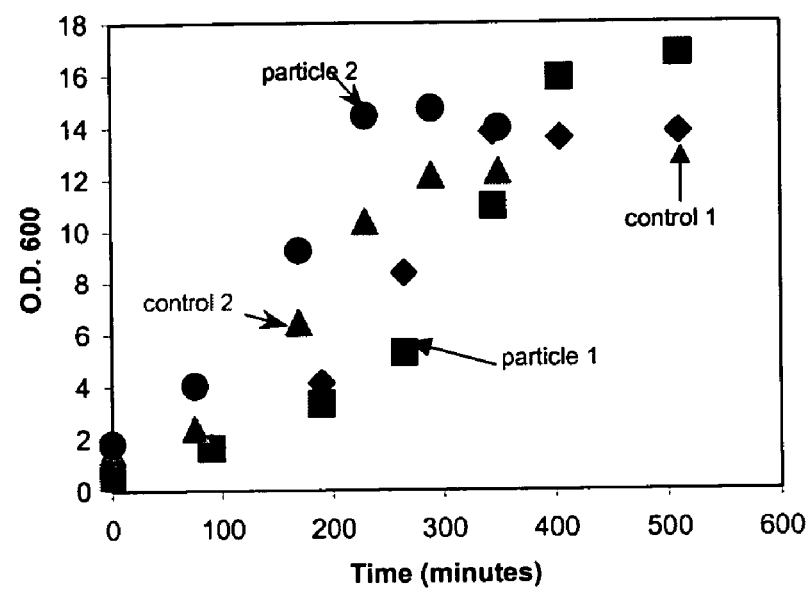
FIG. 4 depicts the results of the toxicity test of the magnetic fluid prepared in Example 5.

Magnetic Fluid with Fluorinated Copolymer, poly(tetrafluoroethylene oxide-co-difluorometylene oxide) α, ω-dicarboxylic Acid Nanoparticles were prepared using the fluorinated copolymer, poly(tetrafluoroethylene oxide-co-difluorometylene oxide) α, ω-dicarboxylic acid (obtained from Aldrich Chemical Corp.) as described in Example 4. Their toxicity was tested as described in Example 5. As seen in FIG. 4, cells in the control experiment in the absence of magnetic fluid start to grow faster than those that are in the presence of magnetic fluid. This is believed to be a result of some possible toxicity that is introduced by monomers that may be present in the medium. But, eventually the cells in the presence of particles grow and reach an even higher concentration. This can be observed better in the second set of experiments where there are clearly more cells in the presence of magnetic particles.

Figure 3:
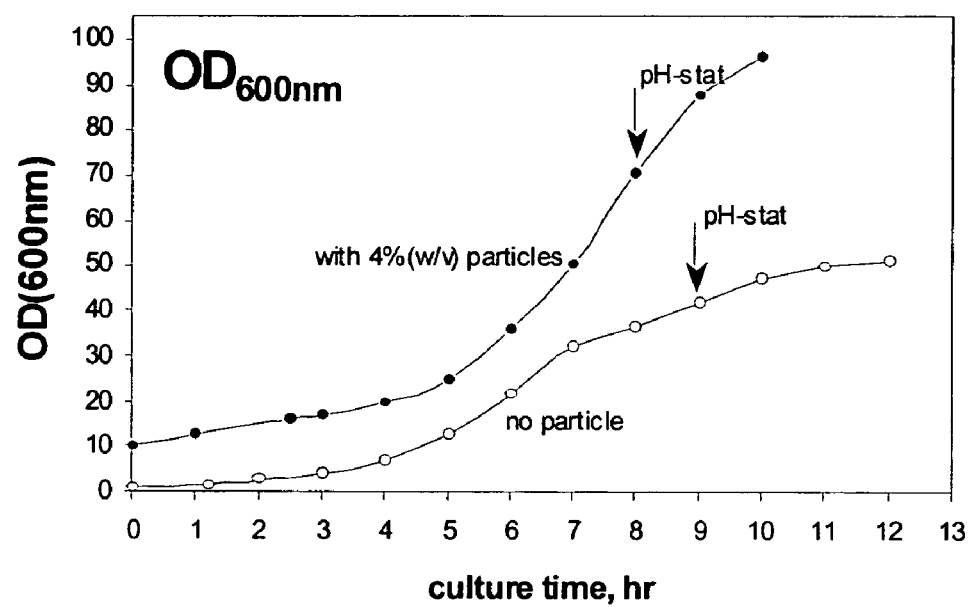
FIG. 3 depicts the effect of fluoropolymer-modified magnetic nanoparticles (4 wt % in fermentation medium) on the *E. coli* cell growth in the fermentation process.

Enhancement of *E. coli* Growth by Fluoropolymer-coated Magnetic Nanoparticles in Fermentation Process A fermentation experiment was conducted to characterize the enhancement-enabling properties of the particles of the present invention. The particles synthesized as described in Example 1 were subjected to fermentation under the experimental conditions presented in Example 3. The main results confirming the cell growth-enhancing properties of the nanoparticles of the present invention are shown in FIG. 3.

Other fermentation experiments using fluoropolymer-modified magnetic nanoparticles have also been conducted. The results are impressive in that the oxygen transfer rate (as measured by the overall mass transfer coefficient) can be increased significantly. The summary of the results from these fermentations are shown below in Table 1. It can be seen from the results in Table 1 that using 2% (w/v) fluoropolymer-modified magnetic nanoparticles, an increase in the overall oxygen transfer over the control fermentation (0%) of 425% and using 4% (w/v) fluoropolymer-modified magnetic nanoparticles, an increase of 443% in the overall mass transfer coefficient were achieved. These increases in the oxygen transfer coefficient would translate to corresponding increased product concentration, for example, recombinant cells or cells producing primary and secondary metabolites.

TABLE 1

Comparison of Oxygen Transfer Coefficient.

| | Particles (w/v) | Air-flow rate (L/min) | OTR = OUR (from 7 to 10 hrs) [mmol $O_2$/(L-h-Atm $O_2$)] | $K_La$ (from 7 to 10 hours) [mmol $O_2$/(L-h-Atm $O_2$)] | Normalized $k_Ls$ (air-flow rate = 2 L/min) [mmol $O_2$/(L-h-Atm $O_2$)] |
|---|---|---|---|---|---|
| Fermentation III | No | 2.0 | 26.68 | 127.0 | 127.0 |
| Fermentation I | No | 3.0 | 36.60 | 172.9 | 131.8 |
| Fermentation II | 2% | 1.0 | 74.04 | 352.6 | 561.0 |
| Fermentation IV | 4% | 2.0 | 122.84 | 585.0 | 585.0 |

OTR = $K_La(C^* - C_L)$;
$k_La = K \cdot (V_s)^{0.67}$;
$C^*$ = 0.21 atm;
K = constant;
$C_L$ = 0 (from 7 to 10 hrs, DO = 0); and
$V_s$ = superficial gas velocity.

The significance of this approach is several fold. First, the increase in the oxygen transfer rate can be accomplished in a conventional agitated and aerated fermentor without any mechanical modification of the fermentor. Secondly, it is believed that any type of fermentor can be used and still attain the increased oxygen transfer rate. For example, another type of fermentor would be a conventional gas-sparged fermentors without mechanical agitation or air-lift fermentors containing a draft tube. These results confirm the enhancement of the cell growth by magnetic nanoparticles of the present invention.

Figure 9:
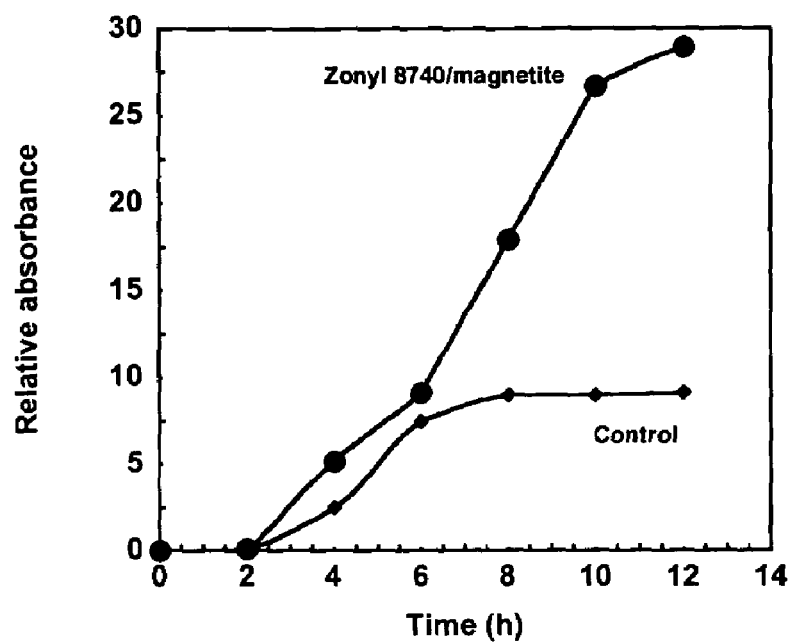
FIG. 9 depicts the results of the tests of the fluoropolymer (Zonyl 8740)-coated magnetic particles in "shake flask" experiments. Control tests were conducted in standard growth media without particle addition. Increase in relative absorbance at 600 nm corresponds to the growth of *E. coli* cells.

The magnetite particles modified by ZONYL 8740 as prepared in Example 8 were also tested for their effect on cell growth in shaken flasks at a 2% particle solids level. The details of the particle testing are given in Example 5. The results of the particle tests are shown in FIG. 9. The results show that the fluoropolymer-modified magnetite particles enhanced the cell growth as evidenced by the 3 times increase in absorbance compared to the control.

Scanning Electron Microscopy (SEM)

Figure 7:
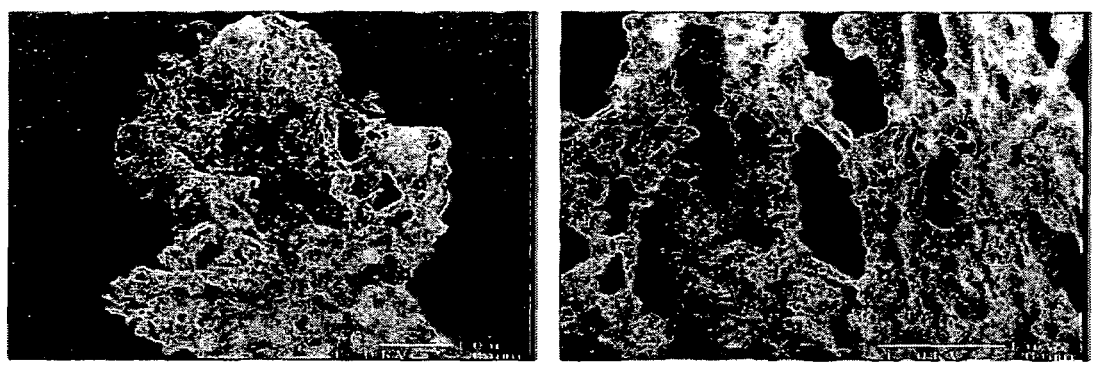
FIG. 7 depicts the SEM microphotographs of the fluorogel consisting of Zonyl® TM, MA, and EGDMA, after grinding, swelling in water and lyophilization.

The fluorogel-coated magnetic nanoparticles and lyophilized fluorogels prepared in Example 7 were studied by SEM. The dried samples were mounted onto a SEM stub with non-conductive glue and sputter-coated with Au/Pd, 100–200 Å. Images of the particles were taken at various magnifications using a JEOL 6320 FE6-SEM microscope. The photographs of the fluorogels without magnetic particles are given in FIG. 7.

As is seen, the fluorogels possess a highly porous structure, which indicates swelling in water. Such structure enables unhindered penetration of dissolved oxygen and other solutes through the fluoropolymer layers, enhancing the oxygen supply in the fermentation processes.

Figure 8:
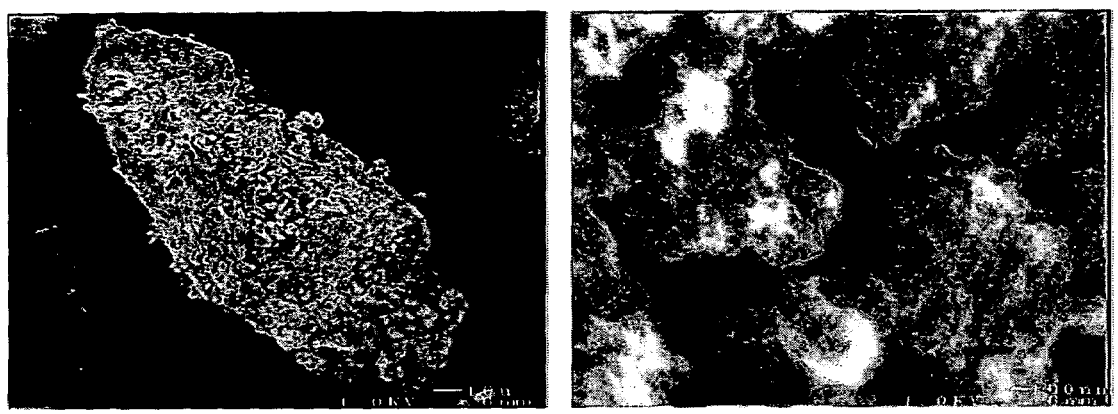
FIG. 8 depicts the SEM microphotographs of the magnetite particles within the fluorogel consisting of Zonyl® TM, MA, and E GDMA, after grinding, swelling in water and lyophilization.

FIG. 8 shows the structure of magnetite particles precipitated within the coagulated fluorogel structures. The magnetite particles are highly crystalline and appear as structured clusters (the right-hand side photo in FIG. 8) within larger polymeric agglomerates.

Hydrocarbon Bilayer: First Hydrocarbon Moiety

In addition to a fluoropolymer, the organic phase of the nanoparticles of the present invention may be a hydrocarbon bilayer. The hydrocarbon bilayer comprises a first and second hydrocarbon moiety chemically bonded to each other.

The first hydrocarbon moiety may be any hydrocarbon that can both bond to the inorganic particle and chemically bond to the second hydrocarbon moiety. The bonding group that bonds the first hydrocarbon moiety to the inorganic particle may be any group that is capable of forming a covalent, ionic, or coordinate (e.g., an interaction between a Lewis base and a Lewis acid) bond to the inorganic compound. When the inorganic compound comprises a metal oxide, the metal is in a positive oxidation state. Metals in a positive oxidation state are almost always Lewis acidic and are therefore able to bind various moieties that may serve as Lewis bases. In general, a moiety serving as a Lewis base will be a strongly acidic group, e.g., with a pKa less than about 7, and more preferably less than 5, which may produce a conjugate base that, under the appropriate conditions, is a strong enough Lewis base to donate an electron pair to a metal ion to form a coordinate bond. The degree of this Lewis acid-to-Lewis base interaction is a function not only of the particular metal ion, but also of the coordinating moiety itself, because the latter may vary in the degree of basicity as well as in size and steric accessibility.

Exemplary Lewis basic moieties comprising oxygen-containing moieties which may be included in the first hydrocarbon moiety include acids, alcohols, alkoxides, ketones, aldehydes, esters, ethers, anhydrides, and the like.

Exemplary Lewis basic moieties comprising sulfur-containing moieties which may be included in the first hydrocarbon moiety include thiols, sulfides, thiocarbonyls (e.g., thiolcarboxyl, thiolester and thiolformyl groups), thioethers, mercaptans, sulfonic acids, sulfoxides, sulfates, sulfonates, sulfones, sulfonamides, sulfamoyls, sulfinyls, and the like.

Exemplary Lewis basic moieties comprising nitrogen-containing moieties which may be included in the first hydrocarbon moiety include amines (primary, secondary, and tertiary) and aromatic amines, amino groups, amido groups, nitro groups, nitroso groups, amino alcohols, nitriles, imino groups, isonitriles, cyanates, isocyanates, carbamoyl groups, and the like.

Exemplary Lewis basic moieties comprising phosphorous-containing moieties which may be included in the first hydrocarbon moiety include phosphates, phosphonates, phosphites, phosphines, phosphine oxides, phosphorothioates, phosphoramidates, phosphonamidites, esters of phosphoric acid, and the like.

Other suitable Lewis bases that may be included in the first hydrocarbon moiety include the following Lewis base functionalities: arsine, stilbines, thioethers, selenoethers, teluroethers, thioketones, imines, phosphinimine, pyridines, pyrazoles, imidazoles, furans, oxazoles, oxazolines, thiophenes, thiazoles, isoxazoles, isothrazoles, amides, alkoxy, aryoxy, selenol, tellurol, siloxy, pyrazoylborates, carboxylate, acyl, amidates, triflates, thiocarboxylate and the like.

The hydrocarbon chain of the first hydrocarbon moiety may be a branched or unbranched hydrocarbon. The hydrocarbon chain may contain heteroatoms within the chain or comprise common organic groups bonded to the chain. The amount of carbon atoms in the hydrocarbon chain may be anywhere from about 4 to about 50, or from about 10 to about 40, or from about 15 to about 30 carbon atoms. The hydrocarbon chain may also comprise aromatic moieties such as an aryl group. The bonding group that bonds the first hydrocarbon moiety to the second hydrocarbon moiety may be any group that is capable of forming a bond covalently, ionically, or coordinatively to the second hydrocarbon moiety. The group may be nucleophilic or electrophilic. When the group is nucleophilic (e.g. amine, hydroxy, thiol etc.) the group on the second hydrocarbon moiety that forms the chemical bond will be electrophilic, and conversely, when the group is electrophilic (e.g. aldehyde, ketone, ester etc.) the group on the second hydrocarbon moiety that forms the chemical bond will be nucleophilic. The bonding group that bonds the first hydrocarbon moiety to the second hydrocarbon moiety may also be an unsaturated carbon-carbon bond. In this case the group on the second hydrocarbon moiety may be any group that can bond with one of the carbons of the unsaturated carbon-carbon bond. For example, the group on the second hydrocarbon moiety may be a nucleophile or it may be another unsaturated carbon-carbon bond. In the former example a carbon-heteroatom covalent bond forms, and in the latter example a carbon-carbon bond forms.

Hydrocarbon Bilayer: Second Hydrocarbon Moiety

The second hydrocarbon moiety is similar to the first in that it comprises a bonding group capable of bonding to the bonding group of the first hydrocarbon moiety, and it comprises a hydrocarbon moiety from about 3 to about 50 carbon atoms. It differs in that instead of a bonding group capable of bonding to the inorganic compound, it comprises a hydrophilic group. The hydrophilic group may be any hydrophilic group commonly known in the art. Hydrophilic groups are generally polar and fall into one of four categories: anionic, cationic, nonionic, and zwitterionic. Non-limiting examples of anionic groups include carboxylates, sulfonates, sulfates, carboxylates, and phosphates. Non-limiting examples of cationic groups include ammonium and quartenary ammoniums. Non-limiting examples of nonionic groups include hydroxy, carbonyl groups such as ketones and aldehydes, polyoxy alkylenes, such as polyoxy ethylene, and polyols, such as sucrose, sorbitan, glycerol, and ethylene glycol. Non-limiting examples of zwitterionic groups include betaines, sulfobetaines, amino acids, and polypeptides. More than one kind of hydrophilic group from more than one category may be combined to form the hydrophilic group. For example, in one embodiment, the hydrophilic group may be an alkylene oxide chain terminating with a sulfonate group. It is believed that the hydrophilic group contributes to the colloidal stability of the nanoparticles in aqueous suspensions.

Reversible Solubilization of a Gas

A unique feature about the nanoparticles of the present invention is that they comprise an organic phase that is capable of reversibly solubilizing a gas. The organic phase may be any organic phase that possesses these characteristics. The organic phase may be homogeneous, comprising one type of compound such as a polymer or copolymer. An example of such an organic phase includes a fluoropolymer or fluoro-copolymer. The organic phase may contain two or more distinct phases comprising two or more compounds, such as a hydrocarbon bilayer. Importantly, the common characteristic between the various types of organic phases is the ability to reversibly solubilize a gas such as, for example, oxygen. It is this ability to reversibly solubilize a gas that makes the nanoparticles of the present invention ideal for various bioprocesses such as fermentation.

There are several methods known in the art for measuring the property of reversibly solubilizing a gas. The following represent non-limiting techniques that can be used to identify and quantify this property.

The first method utilizes a technique that measures oxygen transfer enhancement in cell-free media by use of a gassing-out method (see Example 11).

The aim of this technique is to evaluate how the presence of an organic phase influences the volumetric mass transfer coefficient ($k_L a$) of oxygen in a laboratory system by using a simple gassing-out method and measuring dissolved oxygen concentration.

The experimental equipment is a cylinder-shaped beaker filled with solution (water only or water with the organic phase containing substance). Dissolved oxygen is measured by a dissolved oxygen polarographic sensor (YSI 5010), which is connected to a data acquisition meter (YSI 5100); the dissolved oxygen meter has a built-in barometer that compensates for slight atmospheric pressure variations between runs. The temperature of the beaker is regulated at 37±0.5° C. with a water bath and the pH of the solution is adjusted to 7.0 before the start of the experiment.

Figure 12:
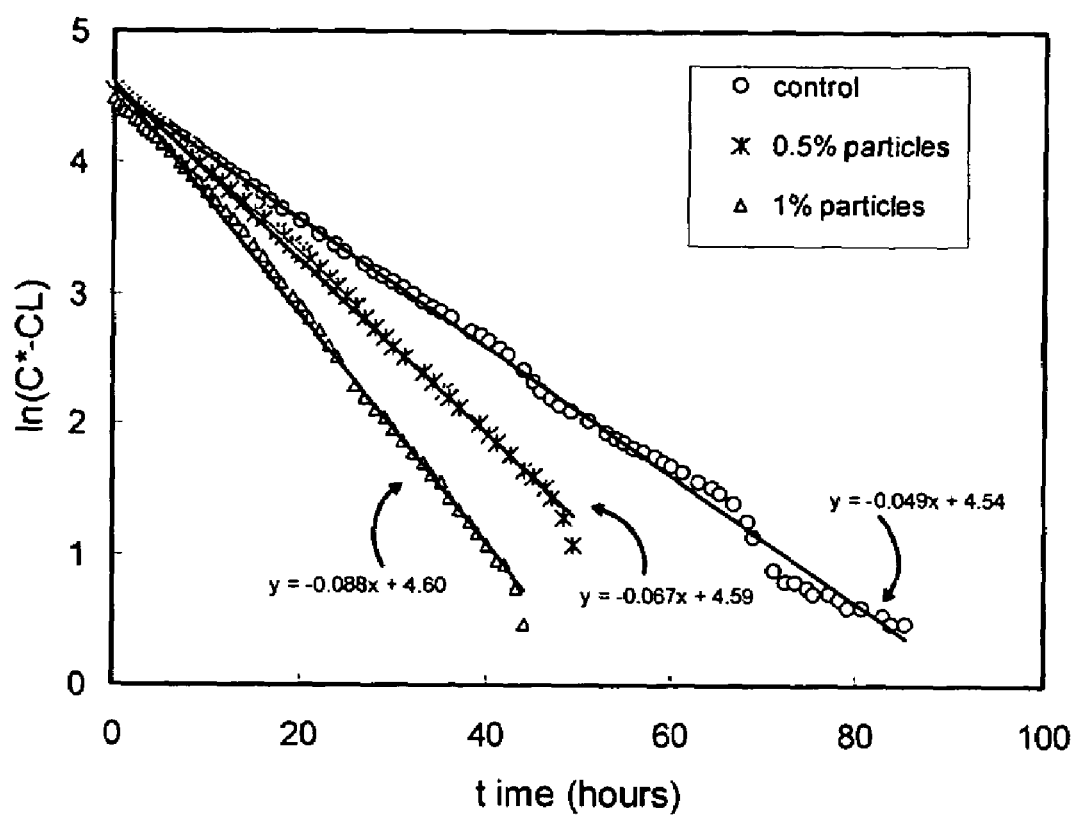
FIG. 12 depicts linearization of the dissolved oxygen response curves at different particle concentrations. The absolute value of the slopes corresponds to the value $k_L a$.

For the organic phase of the nanoparticles of the present invention, the response curves for this technique are shown in FIG. 12 and were obtained by, in a first step, sparging nitrogen until the dissolved oxygen concentration fell to zero and then, in a second step, monitoring the increase of the dissolved oxygen concentration due to exposure of the liquid free surface to the room air; only this second step is shown in FIG. 12. In order to facilitate the study by having a constant gas-liquid interfacial area, no air sparging was used during the second step. The relatively long duration of the experiments (~1 hour) guarantees that the time constant of the probe does not affect the response curves.

Figure 11:
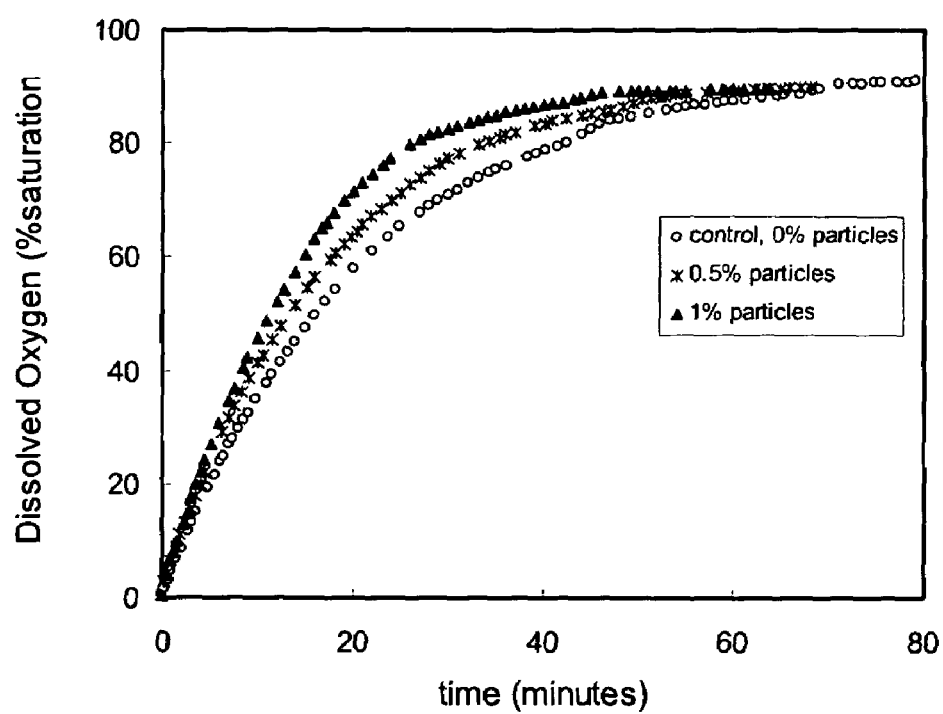
FIG. 11 depicts response curves of dissolved oxygen at increasing magnetic nanoparticle concentrations.

Data in FIG. 11 show that the response time decreases with increasing particle concentration.

In order to quantify the enhancement in the mass transfer coefficient, the following analysis is applied:

Oxygen transfer rate to the liquid phase is described by the general equation $$O.T.R. = k_L a (C^* - C_L) \quad [1]$$

where O.T.R. is the oxygen transfer rate, $k_L$ the mass transfer coefficient of the liquid phase, a the specific surface of the interface, $C^*$ the oxygen concentration at the gas-liquid interface, and $C_L$ the oxygen concentration in the liquid phase.

The integrated form of eq. [1] can be used to calculate $k_L a$ from the response curve data shown in FIG. 12:

$$\ln(C^* - C_L) = -k_L a (C^* - C_L) + R \quad [2]$$

with $C_L = 0$ when $t=0$, and where R is an integration constant. The negative slope of a logarithmic plot of $\ln(C^* - C_L)$ against time corresponds to the value of $k_L a$.

Inspection of the slopes in FIG. 12 reveals that 37% and 80% enhancements in the mass transfer coefficient can be obtained by using 0.5% and 1% particles respectively. These figures have been obtained by dividing the slopes of the 0.5% and 1% curves by the slope of the control.

Another technique characterizes oxygen transfer enhancement in a laboratory scale fermentor by use of a sulfite oxidation method (see Example 13).

The aim of this technique is to evaluate how the presence of an organic phase influences the volumetric mass transfer coefficient ($k_L a$) of oxygen in a laboratory scale, air-sparged fermentor, by using the sodium sulfite method, a well-known approach in the fermentation field. The method is conducted using a sodium sulfite solution, which in the presence of $Cu^{2+}$ catalyst, is oxidized following the reaction $$Na_2SO_3 + 1/2\ O_2 \xrightarrow{Cu^{2+}} Na_2SO_4 \qquad [3]$$

The kinetics of the reaction is independent of the sulfite concentration, and the oxygen consumption rate is fast enough so that oxygen transport form the gas to the liquid, rather than the chemical reaction, is the limiting step. Therefore, $k_L a$ can be calculated by measuring the rate of reaction. Using the nanoparticles of the present invention, this was done by measuring the offgas composition and performing a mass balance on oxygen in the reactor $$\text{Oxygen Uptake Rate} = \frac{(F_{N_2})_{in}\left[\left(\frac{C_{O_2}}{C_{N_2}}\right)_{in} - \left(\frac{C_{O_2}}{C_{N_2}}\right)_{out}\right]}{V} \qquad [4]$$

where $(F_{N_2})_{in}$ is the flowrate of $N_2$ entering the reactor, $C_{O_2}$ and $C_{N_2}$ are the concentrations of oxygen and nitrogen entering or exiting the reactor, and V is the working volume.

The volumetric mass transfer coefficient can then be determined by $$k_L a = \frac{\text{Oxygen Uptake Rate}}{C^* - C_L} \qquad [5]$$

where all the terms in the Eq [5] were previously defined in Eq. [1]. The values of C*, the equilibrium concentration at the gas-liquid interface, correspond to the equilibrium values for the gas outlet; by using this values, it is assumed that the tank is perfectly mixed.

Table 2 summarizes the results obtained in two experiments comprising the nanoparticles of the present invention, one control run without particles, and one run with 1.4% (w/v) of particles. It can be seen that significant enhancements in the mass transfer coefficient can be attained over the range of agitation speed and aeration rate used.

Figure 15:
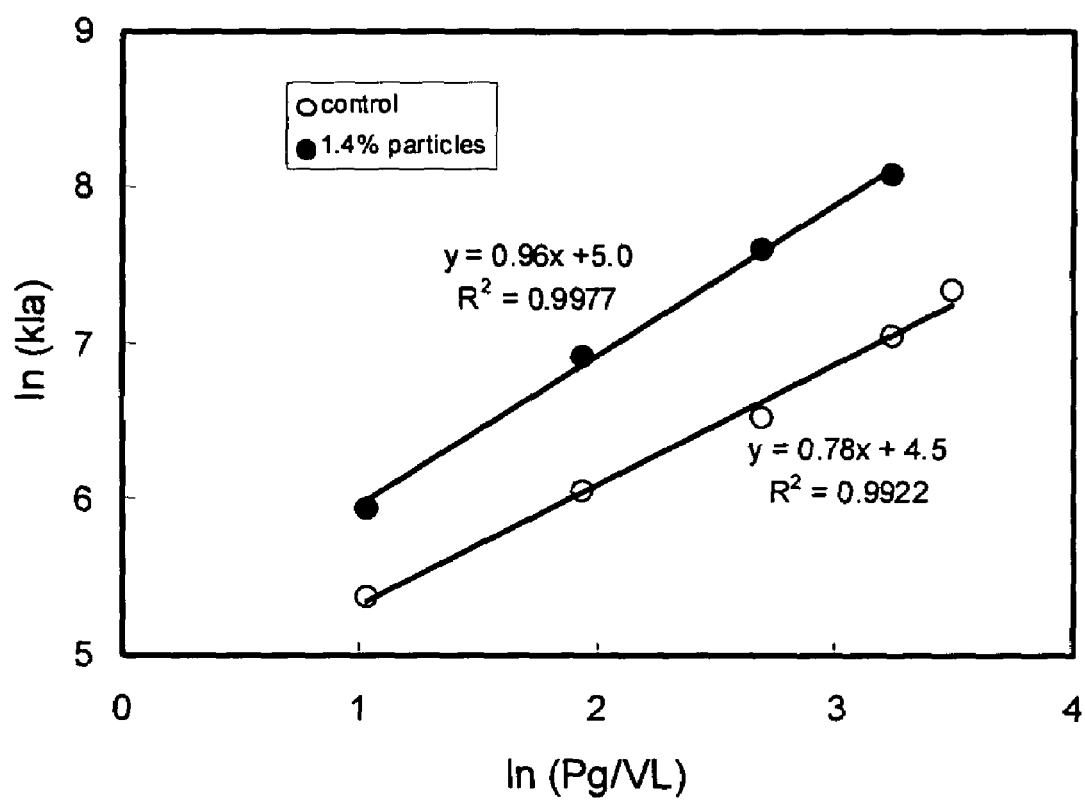
FIG. 15 depicts the correlation obtained for $k_L a$ with power input per unit volume ($P_g/V_L$) in the presence of 1.4% (w/v) particles compared to a control (0% particles). Units of $k_L a$ were mmol/(L*hr*atm), and units of $PG/V_L$ were HP/1000L. Gassed power input was calculated using the aeration number correlation. Oyama, U., Endoh, K., Chem. Eng., 1955, 19, 2.

$K_L a$ measurements were correlated with the power input per unit volume at a constant aeration rate and the functionality obtained is shown in FIG. 15.

A third technique of measuring and quantifying the property of gas solubilization involves a fermentation experiment to characterize the oxygen mass transfer enhancement capacity of an organic phase. The experiment involves measuring the enhancement of cell growth, for example of E. coli, in a fermentation process. A control and experimental fermention process are utilized wherein the experimental process comprises the organic phase containing substance (see Example 14).

Figure 16:
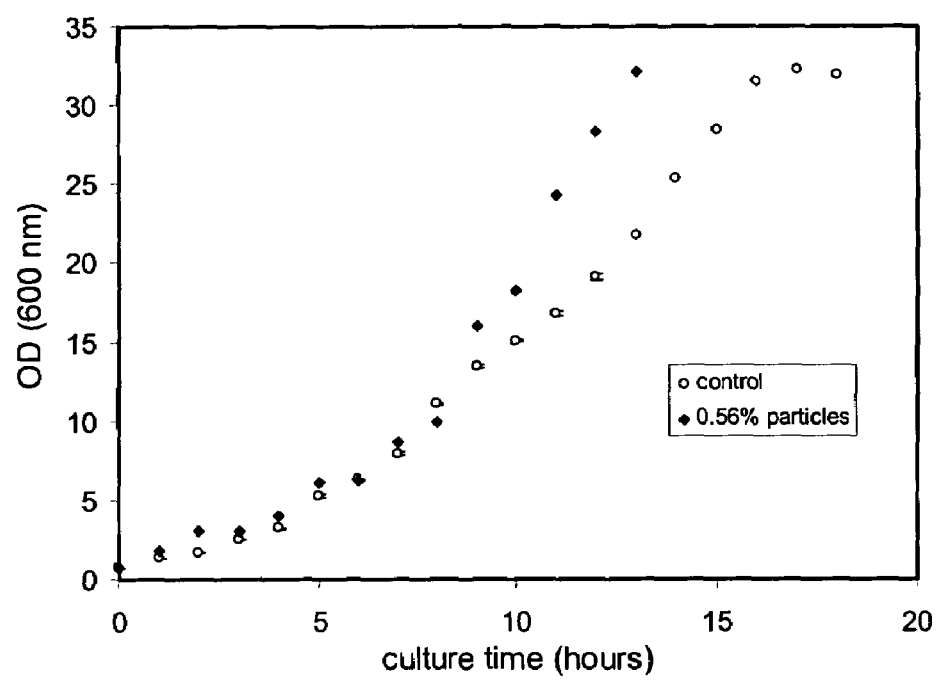
FIG. 16 depicts the optical density versus time for a fermentation using 0.56% (w/v) hydrocarbon-coated magnetic nanoparticles compared to a fermentation done without particles.
Figure 17:
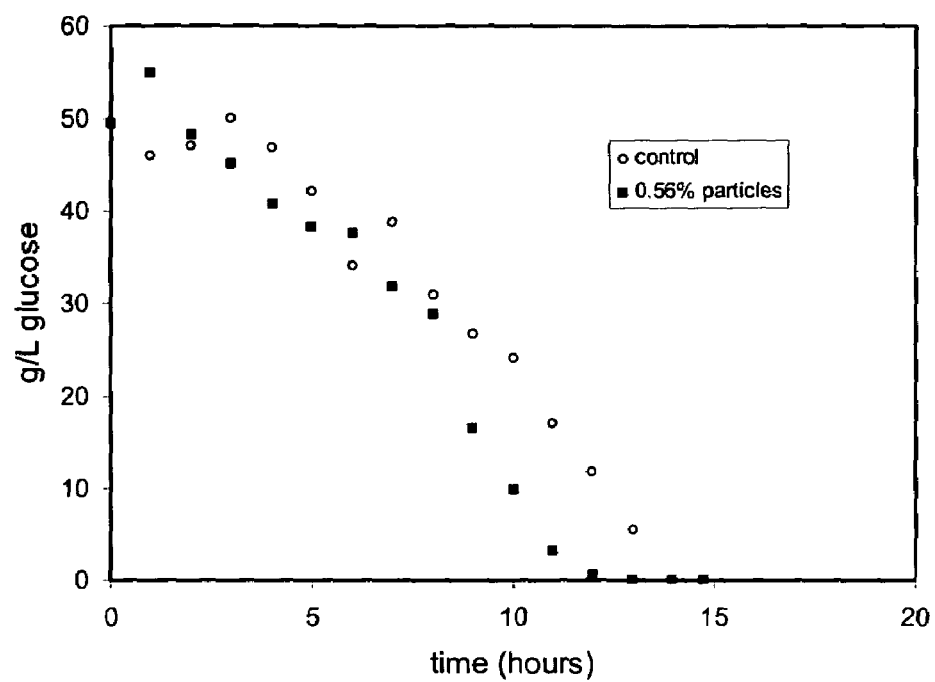
FIG. 17 depicts glucose concentration versus time for a fermentation using 0.56% (w/v) hydrocarbon-coated magnetic nanoparticles compared to a fermentation done without particles.
Figure 18:
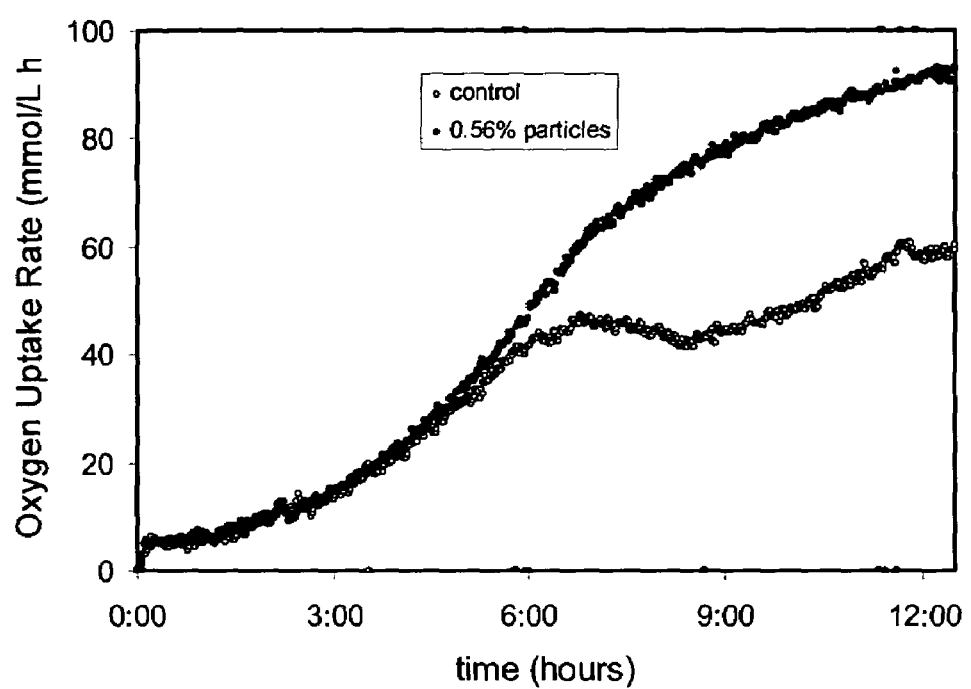
FIG. 18 depicts oxygen uptake rate versus time for a fermentation using 0.56% (w/v) hydrocarbon-coated magnetic nanoparticles compared to a fermentation done without particles.

The results from a fermentation process for the nanoparticles of present invention are shown in FIGS. 16–18. These results confirm the capacity of the particles for improving cell growth by enhancing oxygen mass transfer. FIG. 16 shows that, by using as little as 0.56% (w/v) of magnetic nanoparticles, higher cell growth rates can be maintained when the cultures grow under an oxygen transfer limited regime (in FIG. 16, the oxygen-limited growth onset is at around 5 hours, and both cultures grow under oxygen limitations until the end of the experiments). FIG. 17 corroborates the data from FIG. 16 by showing that, after 5 hours, when the culture grows under oxygen limitations, the glucose consumption, which is indicative of cell proliferation, is faster in the presence of magnetic nanoparticles. Finally, FIG. 17 shows the oxygen uptake rates for the two experiments as calculated from the readings of the offgas analysis, which are measured by a mass spectrometer (Perkin Elmer MGA1600). The total amount of oxygen uptaken by the culture growing in the presence of 0.56% (w/v) particles during oxygen-limited growth is 50% larger than for the control. Accordingly, the volumetric oxygen mass transfer coefficient is 50% larger in the presence of magnetic nanoparticles.

These increases in the oxygen transfer coefficient would translate to corresponding increased product concentration, for example, recombinant cells or cells producing primary and secondary metabolites.

Hence, the increase in the oxygen transfer rate has been accomplished in a conventional agitated and aerated fermentor without any mechanical modification of the fermentor. Secondly, it is our belief the any type of fermentor can be used and still achieve an increased oxygen transfer rate. For example, conventional gas-sparged fermentors without mechanical agitation or air-lift fermentors containing a draft tube. These results confirm the enhancement of the cell growth by magnetic nanoparticles of the present invention.

Non-limiting examples of organic phases capable of reversibly dissolving gases such as oxygen include anionic and cationic surfactants having at least one polar group and wherein the surfactant has at least 10 carbon atoms, and

TABLE 2

Enhancement in the mass transfer coefficient due to use of magnetic nanoparticles measured with the sodium sulfite method at varying agitation and aeration rates.

| AGITATION (RPM) | AIR FLOW RATE (VVM) | $K_L A$ CONTROL | $K_L A$ 1.4% PARTICLES | ENHANCEMENT $\frac{(k_L a)_p - (k_L a)_c}{(k_L a)_c} \times 100$ |
|---|---|---|---|---|
| 300 | 1 | 216 | 383 | 77% |
| 300 | 0.5 | 182 | 417 | 130% |
| 400 | 1 | 422 | 1010 | 139% |
| 500 | 1 | 685 | 2008 | 193% |
| 600 | 1 | 1156 | 3219 | 178% | nonionic surfactants, e.g., an unsaturated fatty acid such as an oleic acid or a salt thereof, a petroleum sulfonate or the salt thereof, a synthetic or natural sulfonate or a salt thereof, polybutene succinic acid or a salt thereof, a polybutene sulfonic acid or a salt thereof, polyoxyethylene nonyl phenyl ether, polymers such as acrylamides or perfluoropolymers and the like.

Additional Applications

In addition to oxygen transfer enhancers, the magnetic nanoparticles and aqueous colloids thereof of the present invention have other promising applications in the medical sciences or biotechnology. Such applications include, but are not limited to, magnetically enhanced cell separation and in vivo drug targeting. In vivo drug targeting may be carried out by selective adsorption of medicines at the coating of magnetic particles which can be enriched subsequently in specific tissue of the body by applying external magnetic fields. This type of directing the magnetic fluids to particular sites within tissue has also been discussed for such promising uses as retina repair treatment.

Equally interesting are the many mechanical applications that make use of magnetic nanoparticles and the magnetic fluids that comprise them. The remarkable properties of the magnetic fluids (long-term stability, high magnetic saturation and initial magnetic susceptibility, low viscosity and vapor pressure, absence of a significant aggregation, stability in gravitation fields, and fair thermal conductivity) result in multiple applications:

1. intensification of the heat transfer;
2. high speed rotary seals with zero linkage and low maintenance, e.g. for hard disk drives ('liquid O-ring);
3. damping element for voice coil in loudspeaker systems;
4. heat carriers;
5. magnetic inks for inkjet printing, e.g. for bar coding and signatures read by magnetic recording technology;
6. magnetic separation on non magnetic materials (recycling technology); and
7. measuring devices, transducers, sensors, etc.

For instance, magnetic fluids offer various opportunities to build several classes of sensors for mechanical, electromagnetic and aero- and hydrodynamic measurements. Rosenzweig, R. E., *Ferrohydrodynamics*, Cambridge Univ. Press 1985; I. Anton, I. De Sabata, L. Vekas, *Application oriented researches on magnetic fluids*, Jour. Mag. Mag. Mater. 85, 219, 1990; K. Raj, B. Moskowitz, R. Casciari, *Advances in ferrofluid technology*, Jour. Mag. Mag. Mater. 149, 174, 1995. In particular, the use of magnetic fluids in accelerometer design and construction is favored, because of some magnetofluidic fulfillment's of the necessary accelerometer elements: mass suspension, elastic constant, inertial mass, proportional damping, magnetofluidic levitation servoloop. M. I. Piso, *Magnetic Liquid Accelerometers*, Rom. Jour. Phys. 47,437, 1995. Several types of accelerometers and inclinometers were achieved, their field of application extending from oilrig survey to basic research. Sensitivities in the range from $10^{-10}$ to 100 ms$^{-2}$, frequency domains from static to several $10^3$ Hz and precision up to 16 bit were obtained. K. Raj, B. Moskowitz, R. Casciari, *Advances inferrofluid technology*, Jour. Mag. Mag. Mater. 149, 174, 1995; M. I. Piso, *Magnetic Liquid Accelerometers*, Rom. Jour. Phys. 47, 437, 1995.

A main characteristic that distinguishes this class of sensors is the significant response to quasistatical and low frequency inertial and gravity variations, a difficult task for most of the common sensors. Relevant performance could be attained in the field of high sensitivity and linearity measurements, the inertial magnetic fluids sensors providing smaller sizes and costs at equivalent performance. For advanced applications as terrestrial tides and seismic monitoring, geophysical surveys, inertial guidance, those sensors are competitive in performance with the superconducting devices. Both linear and angular movement could be sensed by magnetic fluid aided sensors or even by some intrinsic effects of the magnetofluidic material.

Magnetic nanoparticles have also found use in magnetic ink toners for reprographic applications. Reprographic processing involves the formation of printed images on sheet substrates, such as paper. Examples of reprographic processing include the printing of facsimile transmissions, making of photocopies, and printing of electronically stored information from a computer. Technological developments over the last several years have made available high quality, relatively low cost facsimile machines, photocopiers and printers for black print applications. The same low cost, high quality options are not available, however, for color print applications.

High quality color ink jet printers have been introduced in recent years. These printers use a liquid jet spray to form a color image on paper. Although print images are of high quality, the printing process is slow and requires special paper, which increases the cost of the process.

Color laser printers have also been introduced, in which a dry toner is mechanically applied to a drum to develop the desired image. These color laser printers, however, require image-on-image development, with each color being developed separately to create the ultimate desired composite color image. Image-on-image development requires that each separate color image be transferred for storage onto an intermediate device, where the composite image is developed by overlaying individual color images. The finished composite image is then transferred to a piece of paper for printing. Each color is thus developed in a separate step, which significantly slows the printing operation and requires the expense and complications associated with the intermediate storage device.

Fast and relatively inexpensive laser printers are available for black printing that do not require mechanical application of toner to a drum. These printers use "jump gap" technology in which magnetic particles embedded in toner particles assist the toner particles in "jumping" across a gap and onto a drum where the image is developed. Such jump gap processing does not require mechanical application of the toner to the drum. Color printing might be accomplished, therefore, on such a laser printer without the burden and expense of the image-on-image development process of current color laser printers. One problem with adapting the jump gap technology for color printing, however, is that the inherent color of magnetic particles used in the toner significantly dulls and distorts the sharpness of pigments or dyes that may be used in the toner to provide the desired color.

One proposal for reducing the dulling and distortion of color caused by magnetic particles is to use nanoparticle γ-Fe$_2$O$_3$ as the magnetic particles (R. F. Ziolo et al., Matrix-Mediated Synthesis of Nanocrystalline gamma-Fe$_2$O$_3$: A New Optically Transparent Magnetic Material, Science, vol 257, July 1992, pp. 219–223). Due to their small size, it is proposed that such particles would tend to be more transparent than the larger magnetic particles currently used in toner compositions and, therefore, would not distort colors as much as the currently used magnetic particles.

Many more applications can be envisioned by those ordinarily skilled in the art of nanoparticle technology and magnetic properties than those listed above. The above applications are meant to be only exemplary and not limiting in any way.

EXEMPLIFICATION

The invention now being generally described, it will be more readily understood by reference to the following examples, which are included merely for purposes of illustration of certain aspects and embodiments of the present invention, and are not intended to limit the invention.

Example 1

Synthesis of $Fe_3O_4$ Nanoparticles Stabilized by a Fluoropolymer having Weak Acidic Charges The following chemical reaction describes the synthesis:

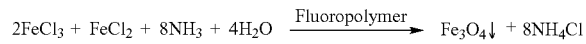

$$2FeCl_3 + FeCl_2 + 8NH_3 + 4H_2O \xrightarrow{Fluoropolymer} Fe_3O_4\downarrow + 8NH_4Cl$$

Deionized water (100 mL) was deaerated by nitrogen bubbling in a 3-necked 1000-mL flask under stirring at ambient temperature. Then 47 g of Fe (III) chloride hexahydrate (Aldrich, 97%, CAS 10025-77-1, Cat.No. 23,648-9, Lot 06029HU, MW 270.30 $FeCl_3 \cdot 6H_2O$) and 17.2 g Fe (II) chloride tetrahydrate (Aldrich, 99%, CAS 13478-10-9, Cat.No. 22, 029-9, Lot #19329LI, MW198.81, $FeCl_2 \cdot 4H_2O$) were added and the flask was stirred under nitrogen flow until salts dissolved and then brought to 80° C. using an oil bath. The nitrogen bubbling was discontinued. When at 80° C., 720 mL of 12.5% solution of Fluorolink™ (pH 14, dispersion:30%$NH_4OH$=1:1 v/v) were added at once while stirring vigorously. The solution quickly turned black. The mixture was kept for 30 min at 80° C. while stirring and then allowed to cool to ambient temperature and disassembled. The suspension of particles was sonicated for about 6 min. The resulting dispersion possessed magnetic properties and was unstable on standing at room temperature overnight. The synthesis was repeated five times, and the resulting fluoropolymer-modified particles were collected to a large batch.

Batches were combined and were left undisturbed to settle at r.t. The precipitate was separated from the supernatant and dried at 60° C. for 3 h. The black mass of particles was diluted by Zonyl FSA (particles:Zonyl 1:1 w/w) and the mixture was left to equilibrate, stirring occasionally, for 4 days.

The viscous solution was loaded into dialysis tubing (MWCO 6–8 kDa) and dialyzed against deionized water for a week, changing water 5 times daily (amount of water per change=20 L, in a bucket).

The resulting particle suspension was sonicated for 10 min and was observed to be stable on standing at room temperature for at least a week without any signs of particle sedimentation. The particles were characterized by high fluorine content (44 wt %) and contained iron (5 wt %). The particles possessed very strong magnetic properties.

Example 2

Benign Nature of Fluoropolymer-coated Magnetic Nanoparticles

The following cell strain and media were used in a shake-flask batch experiment to test the toxicity of the nanoparticles prepared in Example 1:

Strain: *E. coli* BL21 (DE3) with pET-15b(CLP3.1) for the expression of collagen-like polymer CLP3.1.

LB medium for seed culture (/L)

| NaCl | 10 g |
| Tryptone | 10 g |
| Yeast extract | 5 g |

MR medium for fermentation culture (/L)

| $KH_2PO_4$ | 13.5 g |
| $(NH_4)_2HPO_4$ | 4.0 g |
| $MgSO_4 \cdot 7H_2O$ | 0.7 g |
| Citric acid | 0.85 g |
| 10 g/L $FeSO_4 \cdot 7H_2O$ | 10.0 mL |
| Trace metal solution (TE) | 10.0 mL |
| 20 g/L $CaCl_2 \cdot 2H_2O$ | 1.0 mL |

The test comprised the following sequence:
Seed culture
  100 mL LB in 500 mL shake flask.
  overnight culture at 37° C., 220 rpm.
Fermentation culture
  shake flask batch culture
  100 mL MR medium with 20 g/L glucose in 500 mL shake flask
  10% (v/v) inoculation volume
  amount of PCMP: 0, 0.5, 1.0, 2.0, 4.0% (w/v)
  37° C., 220 rpm

Example 3

Enhancement of *E. coli* Growth by Fluoropolymer-coated Magnetic Nanoparticles in Fermentation Process A fermentation experiment was conducted to characterize the enhancement-enabling properties of the particles of the present invention. The particles synthesized as in Example 1 were subjected to fermentation under the following experimental conditions:

Seed culture
  100 mL LB in 500 mL shake flask
  overnight culture at 37° C., 220 rpm
Fermentation culture (7.5 L fermentor)
  inoculation volume: 10% (v/v)
  initial fermentation volume: 3 L
  temperature: 37° C.
  agitation speed: 600 rpm
  pH=6.8–6.9, adjusted by 4 M ($NH_4OH$:NaOH=2:2)

The fermentation was in two stages as follows:
  First Stage: batch culture till glucose decreased to zero (~8 to 9 hours)
  Second Stage: pH-stat fed-batch culture by feeding (500 g/L flucose+10 g/L $MgSO_4 \cdot 7H_2O$)

Example 4

Preparation of Magnetic Fluid with Fluorinated Copolymer, poly(tetrafluoroethylene oxide-co-difluorometylene oxide) α, ω-dicarboxylic Acid The polymer used for modification of iron oxide particles was poly(tetrafluoroethylene oxide-co-difluorometylene oxide) α, ω-dicarboxylic acid obtained from Aldrich Chemical Corp. The polymer possesses 2 carboxylic acid groups on two ends of its chain. It is water insoluble, but dissolves fully in 28–30% $NH_4OH$.

Thirty-five mL of Milli-Q water were de-aerated by passing $N_2$ gas through for about 20 minutes under vigorous stirring. 2.35 g $FeCl_3$ and 0.86 g $FeCl_2$ were added under $N_2$ and the solution was heated to 72° C. with an oil bath that is controlled by a thermocouple. Once the temperature reached 72° C., the $N_2$ line was disconnected and 6 g of the polymer that is dissolved in 10 mL of concentrated $NH_4OH$ were added to the solution very quickly. The reaction was left to proceed for ½ hour at 80° C. under vigorous stirring. Magnetic fluid formation was achieved.

This suspension was then diluted and was passed through magnetic filter to clean the unreacted and thus unwanted free polymer from the medium. To concentrate the magnetic fluid solution, ultracentrifuge dialysis membranes were used with a 10,000 molecular weight cut-off.

Example 5

Toxicity Studies with Magnetic Fluid Prepared as in Example 4

Control 1

Three portions of 25 mL of MR medium (as described above in Examples 2 and 3) were put in three 250 mL culture flasks and the flasks were autoclaved. After autoclave, 2 mL of filtered (through 1 μm pores) glucose (500 g/L) was added to each flask. 50 μL of antibiotic was added to each flask. 3 mL of seed culture (see Examples 3 and 4) were added to each flask to make 10% solution.

Particle 1

Same as Control 1, but instead of 25 mL MR medium, 22 mL MR medium and 3 mL 1 wt % MF were added.

Control 2

Three 27 mL of MR medium were autoclaved in 250 mL flasks. 3 mL of Control 1 solution after 10 hours is added to the MR medium.

Particle 2

Three 24 mL of MR medium and 3 mL MF solution were autoclaved in 250 mL flasks. 3 mL of Particle 1 solution after 10 hours is added to the MR medium.

Example 6

Synthesis of $Fe_3O_4$ Nanoparticles Stabilized by a Fluoropolymer having Strongly Acidic Charges This Example illustrates synthesis and properties of magnetic nanoparticles modified by already prepared fluoropolymer having strong acidic, sulfonic groups.

The chemical reaction describing the synthesis is generally analogous to the one in Example 1. Namely, the magnetite nanoparticles are synthesized by precipitation from the $Fe^{3+}/Fe^{2+}$ aqueous solution in the presence of ammonia and a specific fluoropolymer. The fluoropolymer used in the present Example was perfluorosulfonic acid/tetrafluoroethene copolymer, obtained under trade mark Nafion® Dispersion from DuPont Fluoroproducts (Wilmington, Del.). The Nafion® resins are the products of copolymerization reactions of tetrafluoroethene (TFE) and trifluorovinyl ethers possessing perfluoroalkylsulfonyl fluoride side-chains that are converted to sulfonic acid products after hydrolysis:

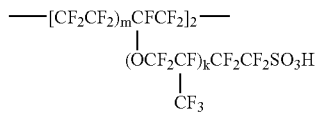

A series of syntheses was conducted with the aim of evaluating the most appropriate Nafion® resins that cause no dramatic coagulation of the magnetic nanoparticles under the synthesis conditions. When a solution of Nafion® (eq MW 1,100) in a mixture of lower aliphatic alcohols and water (Aldrich 52,712-2, lot#10723EO, CAS 31175-20-9) was applied, the resulting precipitates were large (several millimeters in diameter) rubbery aggregates that were impossible to grind and were hardly water-dispersible. However, it was discovered that an aqueous dispersion of Nafion® (Type DE1021, lot #SG01-002) results in an appropriate product as described below.

Deionized water (30 mL) was deaerated by nitrogen bubbling in a 3-necked 500-ml flask under stirring at ambient temperature. Then 14.1 g of Fe (III) chloride hexahydrate (Sigma-Aldrich, 98%, CAS 10025-77-1, Cat. No. 207926, batch#12806BA, MW 270.30 $FeCl_3.6H_2O$) and 5.16 g Fe (II) chloride tetrahydrate (Aldrich, 99%, CAS 13478-10-9, Cat. No. 22, 029-9, Lot #16324JO, MW198.81, $FeCl_2.4H_2O$) were added and the flask was stirred under nitrogen flow until salts dissolved and then brought to 80° C. using an oil bath. The nitrogen bubbling was discontinued. When at 80° C., a mixture of 12% solution of Nafion® (200 mL, DuPont Type DE1021, lot #SG01-002) and 50 mL of 28% $NH_4OH$ aqueous solution were added at once while stirring vigorously. The suspension quickly turned black. The mixture was kept for 2 h min at 80° C. while stirring and then allowed to cool to ambient temperature and the flask was disassembled. The suspension of particles w as sonicated for about 15 min. The resulting fine dispersion was dried at 90° C. until constant weight. The resulting particles were strongly magnetic and were of about 2–10 μm average size. A population of magnetic precipitates of 8–10 nm size was observed within the fluorocarbon-coated particles by scanning electron microscopy. Measurements of ζ-potential were conducted in a 200 ppm microparticle suspension in 1 mM KCl at ambient temperature, adjusting the pH by 5M HCl or NaOH. The ζ-potential measurements yielded −18.35±0.67, −17.95±0.50, and −19.05±0.65 mV at pH of 1.9, 6.5, and 12.4, respectively. That is, the ζ-potential was negative and pH-independent, indicating the presence of the strongly acidic groups on the particles surface. The negative charge keeps the suspension colloidally stable for the duration of the fermentation experiment.

Example 7

Synthesis of $Fe_3O_4$ Nanoparticles Modified by a Fluoropolymer Prepared In Situ This Example illustrates the method of preparation of magnetic nanoparticles modified by a copolymer prepared by free-radical polymerization occurring simultaneously with the magnetic particle precipitation.

The design of the copolymer involves several vinyl monomers: a hydrophobic fluorine-containing monomer, 2-(perfluoroalkyl)ethylmethacrylate (Zonyl®™), a chargeable monomer, methacrylic acid (MA), and a cross-linker, ethylene glycol dimethacrylate (EGDMA):

Zonyl®™; n=8, $M_n$ 534, fluorine content 60%

Methacrylic acid

[CH$_2$=C(CH$_3$)COOCH$_2$—]$_2$

Ethylene glycol dimethacrylate

The synthesis is conducted by dissolving all the monomers in chloroform, which is found to be a good common solvent. The solution is emulsified in water using perfluorododecanoic acid as emulsion stabilizer. The polymerization is initiated by a zobisisobutyronitrile (AIBN). The resulting copolymer is a cross-linked gel. The detailed description of the synthesis is given below.

Deionized water (20 mL) was deaerated by N$_2$ bubbling in a 3-necked 1000-mL flask under stirring at ambient temperature. Then 1.41 g of Fe (III) chloride hexahydrate (Aldrich, 98%, CAS 10025-77-1, Cat. No. 23,648-9, Batch 12806BA, MW 270.30 FeCl$_3$.6H$_2$O) and 0.516 g Fe (II) chloride tetrahydrate (Aldrich, 99%, CAS 13478-10-9, Cat. No. 22, 029-9, Lot #16324JO, MW198.81, FeCl$_2$.4H$_2$O) were added and the flask was stirred under N$_2$ flow until salts dissolved and then brought to 80° C. using an oil bath.

Separately, a mixture of 3.0 g Zonyl® ™ (CAS 65530-66-7, Cat.# 42,148-0, lot# C5223BU), 400 μL methacrylic acid, 400 μL ethyleneglycol dimethacrylate, 150 mg azoisobutyronitrile (all of these from Aldrich), 2 mL chloroform, and 10 mg perfluorododecanoic acid (PN2121-3-29, Lot#7C-67, CAS 307-55-1) and 3 mL of NH$_4$OH (28%) was prepared. After mixing, the solution was briefly sonicated to result in emulsion.

When at 80° C., the above emulsion was added to the above iron chloride solution while stirring vigorously under nitrogen blanket. The solution quickly turned black. The mixture was kept for 2 h at 80° C. while stirring and N$_2$ bubbling and then allowed to cool to ambient temperature and the reactor was disassembled.

Formation of black, powdery, almost dry precipitates was observed. The precipitates were suspended in 10 mL DI water and sonicated resulting in a heterogeneous suspension that was stable for several hours. The suspension exhibited strong magnetic properties. The suspension was dried at 90° C. until constant weight, ground up using mortar and pestle, and stored at room temperature.

In a separate series of experiments, an identical procedure but without addition of iron chlorides was conducted, resulting in strong transparent gel particles. The gel particles were dried, ground up using mortar and pestle, suspended in water and lyophilized.

Measurements of ζ-potential were conducted in a 200 ppm microparticle suspension in 1 mM KCl at ambient temperature, adjusting the pH by 5M HCl or NaOH. The ζ-potential measurements on a suspension of the fluorogel-modified particles yielded 0.35±0.42, −12.56±0.78, and −18.05±1.24 mV at pH of 1.9, 6.5, and 12.4, respectively. That is, the ζ-potential was negative at neutral pH, suggesting colloidal stability at pH typical of fermentation processes. The pH-dependence of the ζ-potential indicates the presence of weakly acidic carboxyl groups on the particle surface.

Example 8

Synthesis of Fe$_3$O$_4$ Nanoparticles Modified by a Commercially Available Fluoropolymer A solution of 70.5 g FeCl$_3$.6H$_2$O and 25.8 g FeCl$_2$-nH$_2$O in 100 g deionized water was brought to 80° C., under continuous purging by nitrogen. Then 330 mL of ZONYL 8740 (Pefluoroalkyl methacrylic copolymer, 30% solids) Dispersion in water (DuPont, Lot #66, pH 4) were added and the resulting suspension was kept at 80° C. for 1 h. An aqueous solution of NH$_4$OH was then added (28%, 200 mL) to the dispersion and formation of black precipitates was immediately observed. The precipitates were dried at 80° C. and pulverized by mortar and pestle.

Example 9

Synthesis of Magnetic Nanoparticles Coated by Covalently Bonded Organic Layers.

This Example illustrates a process of preparation of the colloidally stable magnetic nanoparticles wherein the extreme colloidal stability is due to the presence, in the second organic layer covalently bonded to the first hydrocarbon layer, of hydrophilic moieties containing both poly (ethylene oxide) and sulfonate groups.

A solution of 94 g FeCl$_3$.6H$_2$O and 34.4 g FeCl$_2$.4H$_2$O in 100 g water was stirred at 80° C. under nitrogen blanket for 30 min. Then a paste-like dispersion of 40% potassium oleate in water (Aldrich, CAS 143-18-0, pH 12.5) (100 g) was added and the resulting mixture was stirred at 80° C. for 30 min. A viscous brownish suspension formed. Then an aqueous solution of 28% NH$_4$OH (100 mL) was added to the mixture, causing precipitation of magnetic nanoparticles, black in color, coated by oleic acid. The reaction was allowed to proceed at 80° C. under stirring and N$_2$ bubbling for 30 min. Then a dispersion of Hitenol BC-10 (Daiichi Kogyo Seiyaki, Lot #044760) (100 g) was added to the coated magnetic nanoparticles. While continuing stirring and bubbling, a freshly prepared solution of ammonium persulfate (5 g in 20 mL water) was added to the reaction mixture. The reaction was at 80° C. under nitrogen blanket and vigorous stirring for 2 h, allowing for covalent bonding of the propenyl group of Hitenol and the double bond in the alkyl chain of the oleic acid to react. The reactors was then cooled the reactor to r.t. and disassembled. Formation of strongly magnetic, colloidally stable black-brown fluid was observed. The dispersion was dialyzed against dialyzed water and dried at 70° C. The resulting particles were redispersed in water, where they exhibited colloidal stability in water at any pH and in the presence of fermentation broths. Chemical formula of Hitenol BC-10 is shown in Scheme 1, which shows the presence of poly(ethylene oxide groups) and sulfonate groups providing for the colloidal stability of the synthesized magnetite.

Scheme 1.
Structure of the colloidally stable magnetic particles.

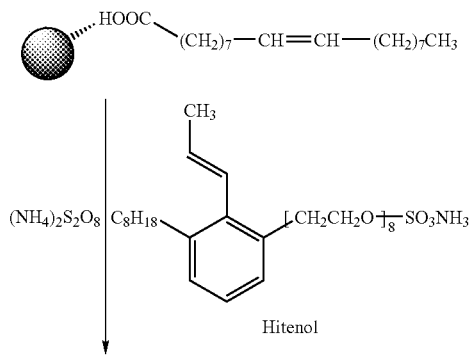

-continued

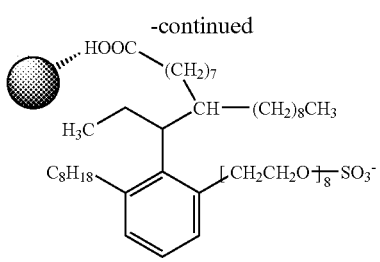

Example 10

Characterization of the Nanoparticles Described in Example 9

Figure 10:
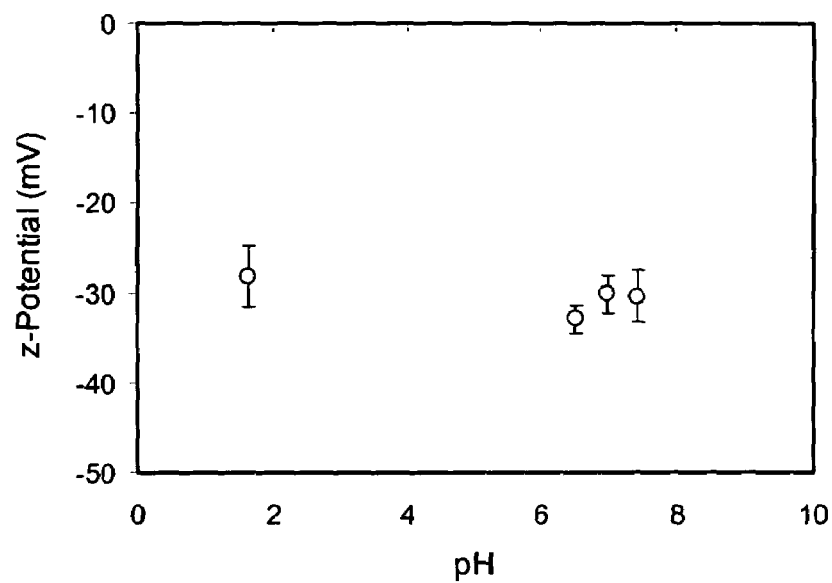
FIG. 10 depicts ζ-potential and number-average diameter of magnetic nanoparticles modified by hydrocarbons and Hitenol as a function of pH as described in Example 9.
Figure 10:
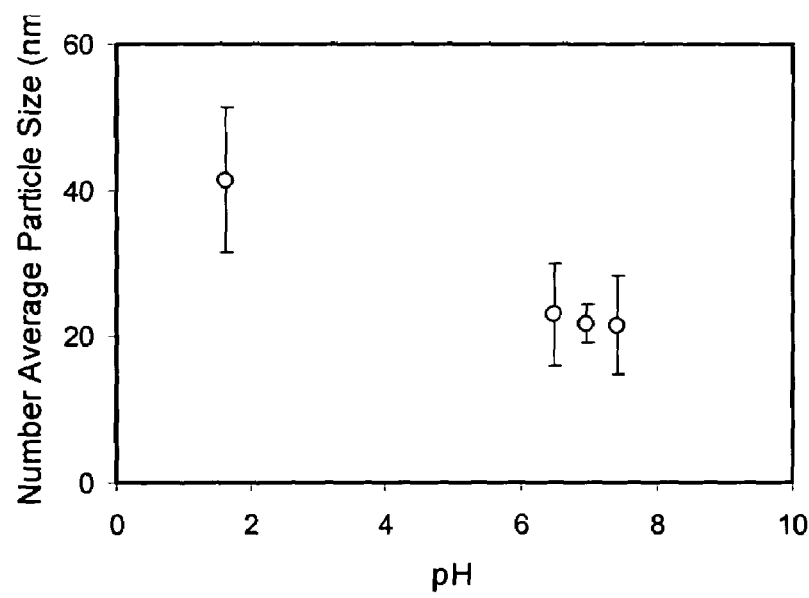

The magnetic nanoparticles described in Example 9 were characterized for their size by dynamic light scattering (Brookhaven Instruments Co.) and for electrophoretic properties by the ZetaPals Zeta Potential Analyzer (Brookhaven Instruments Co.) with a built-in software that employs Smoluchowski $\zeta$-potential model. The results are shown in FIG. 10. It can be seen that the particles exhibit a number-average diameter of about 20 nm and a negative surface charge in a very wide range of pH, including typical pH for bioprocesses (around 7). The particles are thus charge-stabilized and can stay dispersed indefinitely. Measurements of $\zeta$-potential were conducted in 1000 ppm nanoparticle suspensions in 1 mM KCl at ambient temperature, adjusting the pH by acetic acid or NaOH.

Example 11

Characterization of Oxygen Transfer Enhancement in Cell-free Media by Use of a Gassing-out Method The experimental equipment is a cylinder-shaped 250 mL-beaker filled with 200 mL of solution (water only or water with magnetic nanoparticles). Dissolved oxygen is measured by a dissolved oxygen polarographic sensor (YSI 5010), which is connected to a data acquisition meter (YSI 5100); the dissolved oxygen meter has a built-in barometer that compensates for slight atmospheric pressure variations between runs. The temperature of the beaker is regulated at 37±0.5° C. with a water bath and the pH of the solution is adjusted to 7.0 before the start of the experiment.

Results are shown in FIG. 12 and were obtained by, in a first step, sparging nitrogen until the dissolved oxygen concentration fell to zero and then, in a second step, monitoring the increase of the dissolved oxygen concentration due to exposure of the liquid free surface to the room air; only this second step is shown in FIG. 12. In order to facilitate the study by having a constant gas-liquid interfacial area, no air sparging was used during the second step. The relatively long duration o f the experiments (~1 hour) guarantees that the time constant of the probe does not affect the response curves.

Data in FIG. 11 show that the response time decreases with increasing particle concentration.

Example 12

Benign Nature of Hydrocarbon-Coated Magnetic Nanoparticles

The toxicity to *E. coli* cells of the nanoparticles synthesized as described in Example 9 was tested in shake-flask experiments. The *E. Coli* strain used was BL21(DE3) [pUC18]. Initially, a seed culture was done in LB medium, which had the following composition (/L): 10 g NaCL, 10 g tryptone, 5 g yeast extract. *E. Coli* cells were grown in 100 mL of LB medium in a 500 mL shake flask overnight at 37° C. and 220 rpm. Subsequently, the seed culture was pipeted into 500 mL shake flasks contaning MR medium for fermentation culture. Each flask contained 100 mL of MR medium with 15 g/L of glucose and 10%(v/v) of inoculated seed culture. The MR medium had the following composition (/L): 13.5 g $KH_2PO_4$, 4.0 g $(NH_4)_2HPO_4$, 0.7 g $MgSO_4.7H_2O$, 0.85 g Citric acid, 10 mL of 10 g/L $FeSO_4.7H_2O$, 10.0 mL of trace metal solution (TE) and 1.0 mL 20 g/L $CaCl_2.2H_2O$. Each flask also contained a different amount of magnetic nanoparticles, with the following concentrations: 0% (control), 0.5%, 1%, 2%, for a total of 4 flasks The fermentation culture with the four flasks was performed at 37° C. and 220 rpm. The optical density at 600 rn was measured with a spectrophotometer (Hewlett Packard 8452A), and provided a measure of cell growth.

Figure 13:
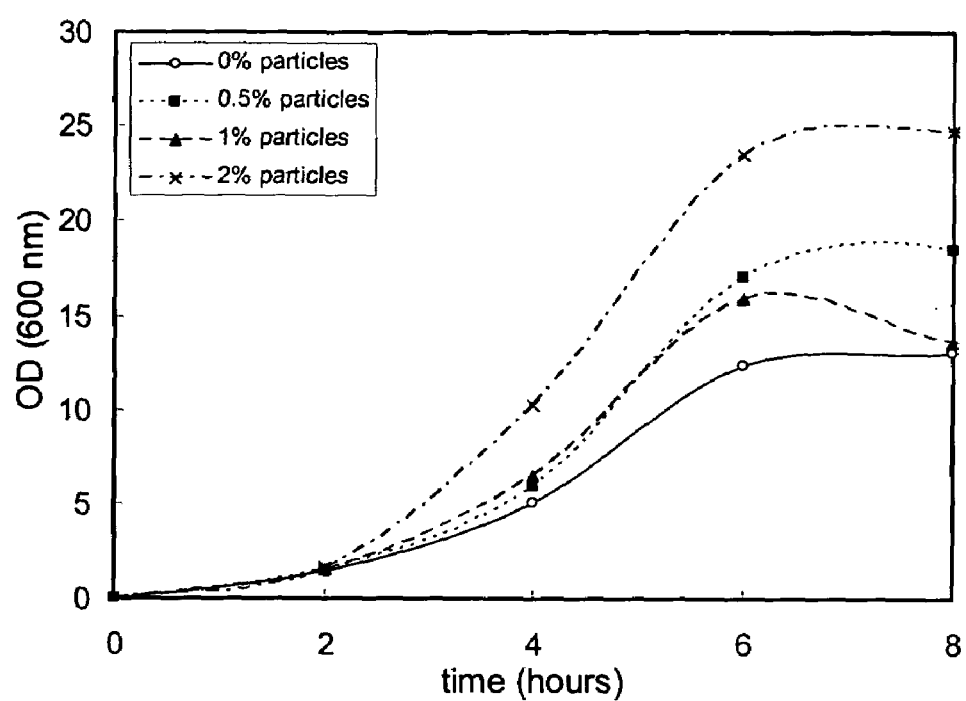
FIG. 13 depicts the toxicity test of the particles synthesized as described in Example 9. *E. coli* cell growth was monitored by measuring optical density at 600 nm.
Figure 14:
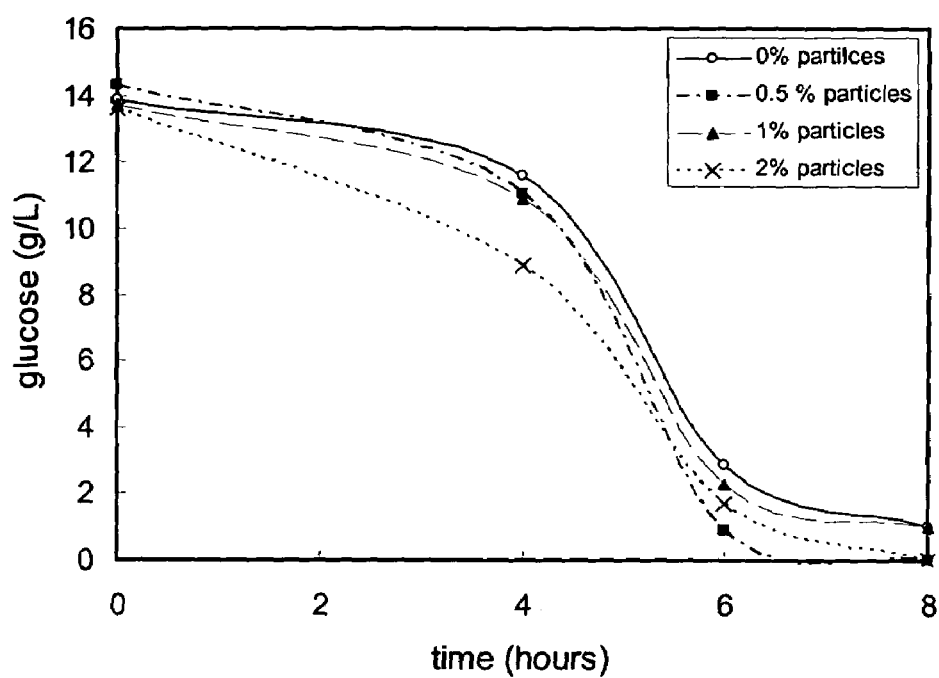
FIG. 14 depicts the toxicity test of the particles synthesized as described in Example 9. Glucose consumption is indicative of cell proliferation.

As shown in FIGS. 13 and 14, the hydrocarbon-coated magnetic particles are non-toxic and do not inhibit cell growth.

Example 13

Characterization of Oxygen Transfer Enhancement in a Laboratory Scale Fermentor by Use of the Sulfite Oxidation Method Experiments were performed in a 20 L (5.5 L working volume) stirred tank reactor (Biolafitte fermentor system, model BL 20.2), which was equipped with an Ingold type pH electrode, a dissolved oxygen electrode (Biolafitte) and a temperature probe. The tank had a bottom aeration consisting of a 4-branded rotating sparger, and agitation was done by a 33-bladed turbine agitator. Initially, a 0.67M sodium sulfite solution was fed to the reactor, and then a $1\times10^{-3}$M solution of copper sulfate catalyst was added. pH was initially adjusted around 8.0 with sulfuric acid to avoid the accelerated reaction regime typical of sodium sulfite solutions at higher pH. Temperature was maintained at 37±0.5° C. The quantity of sodium sulfite added was enough to maintain the dissolved oxygen concentration close to zero for a long time period. An experimental condition, hereby defined as a given agitation speed and a given aeration rate, was chosen, and offgas compostions were recorded using a mass spectrometer (Perkin Elmer MGA 1600). When the values of the offgas compositon stabilized, a value for the mass transfer coefficient was calculated using Eq. [4] and [5]. This procedure was repeated at different experimental conditions.

Example 14

Enhancement of *E. coli* Growth by Hydrocarbon-coated Magnetic Nanoparticles in a Fermentation Process A fermentation experiment was conducted to characterize the oxygen mass transfer enhancement capacity of the particles described in the present invention. A concentration of 0.56% (w/v) of magnetic nanoparticles synthesized as in Example 9 was used in a fermentation that was done under the following experimental conditions:
First, a seed culture was done in 5, 500-ml shake flasks, containing 100 mL of LB medium each, cultured overnight at 37° C. and 220 rpm;

Second, a fermentation culture was performed in a 20 L fermentor (5.5 L working volume).

The inoculation volume was 10% (v/v) from the seed culture, and the temperature, pH, aeration rate, and agitation were controlled at 37° C., 7.0±0.1, 5.0 slpm, and 300 rpm respectively. The fermentation was done in batch mode, starting with a glucose concentration of 50 g/L and proceeding until this concentration decreased to zero. The medium used was the same MR medium as in Example 12, with the addition of 50 μg/ml of ampicillin. Throughout the experiment, foaming due to extracellular products generated by the cells metabolism and also due to the particles, was controlled using a combination of DOW Corning Q7-2243 and SIGMA 204 Antifoams.

Example 15

Synthesis of Magnetic Nanoparticles Coated by Covalently Bonded Organic Layers Capable of Transferring Carbon Dioxide A solution of 47 g $FeCl_3.6H_2O$ and 17.2 g $FeCl_2.4H_2O$ in 100 g water was stirred under nitrogen blanket for 30 min. Then a solution of potassium oleate in water (100 g, 20%) (Aldrich, CAS 143-18-0, pH adjusted from 12.5 to 7.0 by glacial acetic acid) was added and the resulting mixture was stirred at 80° C. for 30 min. A viscous brownish suspension ensued. Then a 75% solution of [2-(methacryloxy)ethyl]-trimethylammonium chloride (Aldrich, MW 207.7, d=1.105, CAS 5039-78-1) (100 mL) was added to the mixture. While continuing stirring and bubbling, an aqueous solution of 4 g ammonium persulfate in water (10 mL total) was added to the mixture and the resulting suspension was kept for 1 h at 80° C. under stirring. Then 50 mL of 28% $NH_4OH$ aqueous solution were added, causing change of the dispersion in color to black. The reaction was allowed to proceed at 80° C. under stirring and nitrogen bubbling for 30 min, the reactor was the cooled to ambient temperature and disassembled. Formation of strongly magnetic fluid was observed. The fluid exhibited infinite colloidal stability at ambient temperature.

Example 16

Transfer of Carbon Dioxide by Magnetic Particles

A 10% solution in water of the magnetic nanoparticles synthesized as described in Example 15, in 100 mM NaCl, was prepared. The pH of the solution was initially adjusted to 12.5 by NaOH. 500 mL of this solution were sparged with $CO_2$ (Identification Number UN1013) in a 600 mL beaker under agitation at a constant temperature of 23.4° C., and the change in pH due to the absorption of $CO_2$ was recorded with a pH probe (Beckman φTM40). In aqueous solution, carbon dioxide exists in different forms. First, it dissolves:

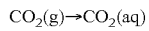

Then, an equilibrium is established between dissolved $CO_2$ and $H_2CO_3$, carbonic acid:

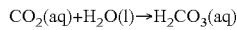

Figure 19:
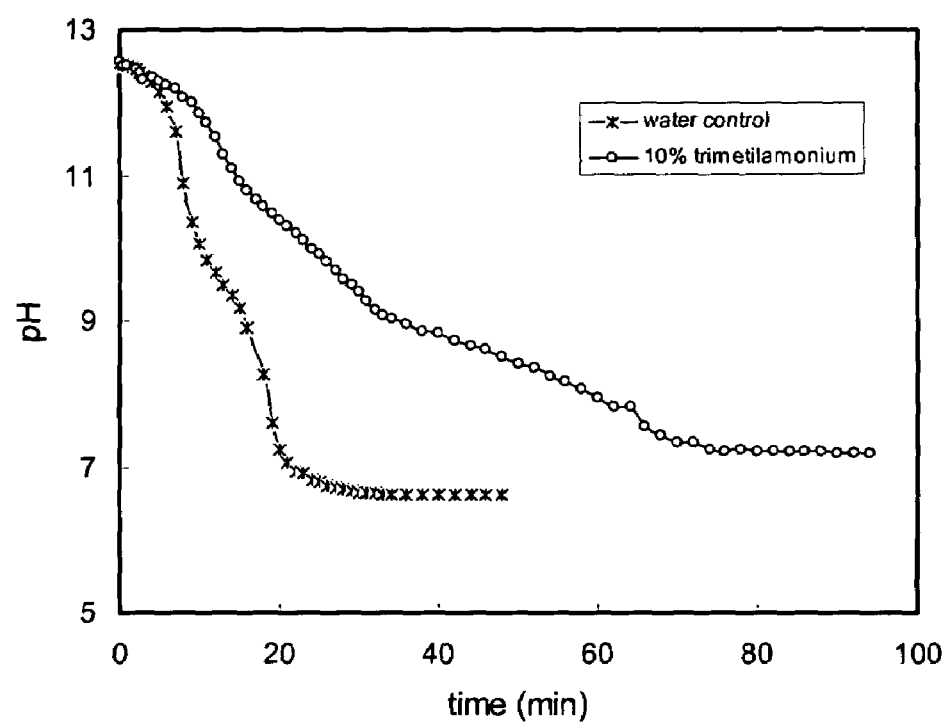
FIG. 19 depicts change of pH with time due to $CO_2$ sparging for a 10% solution in water of magnetic nanoparticles prepared as described in Example 16 and for a water control without particles.
Figure 20:
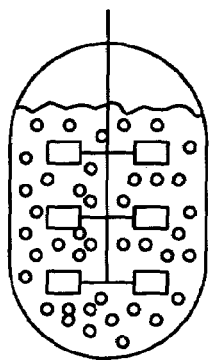
FIG. 20 depicts oxygen transfer in fermentation and some related parameters and measurements.
Figure 21:
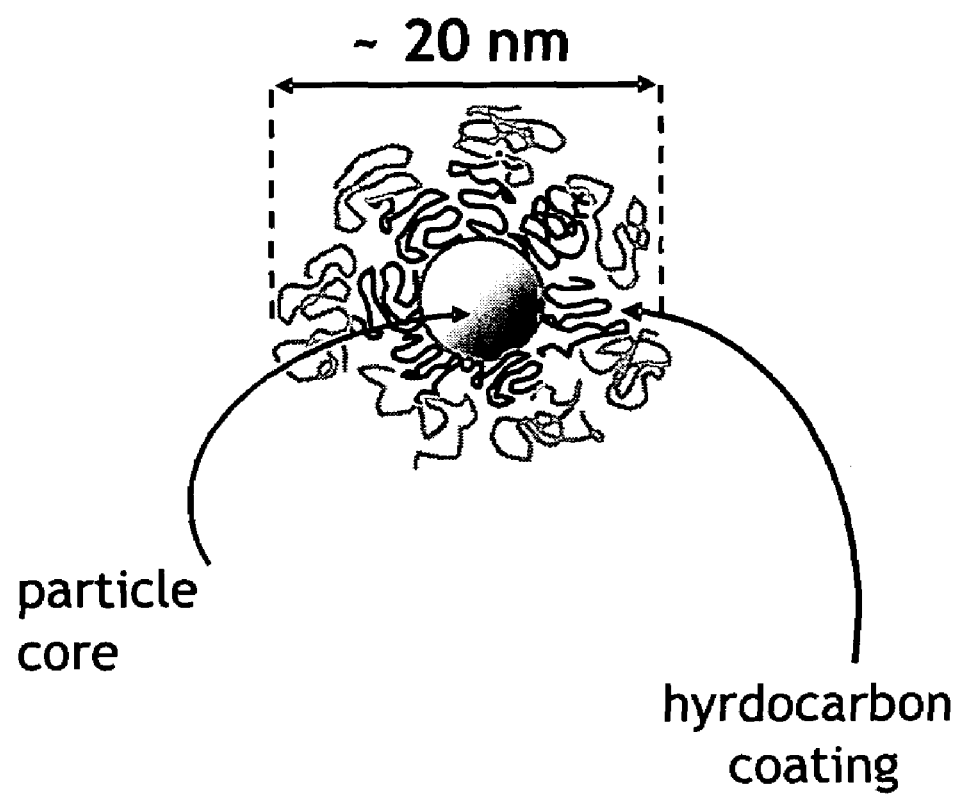
FIG. 21 depicts one embodiment of the present invention, wherein the core is associated with a hydrocarbon bilayer.
Figure 22:
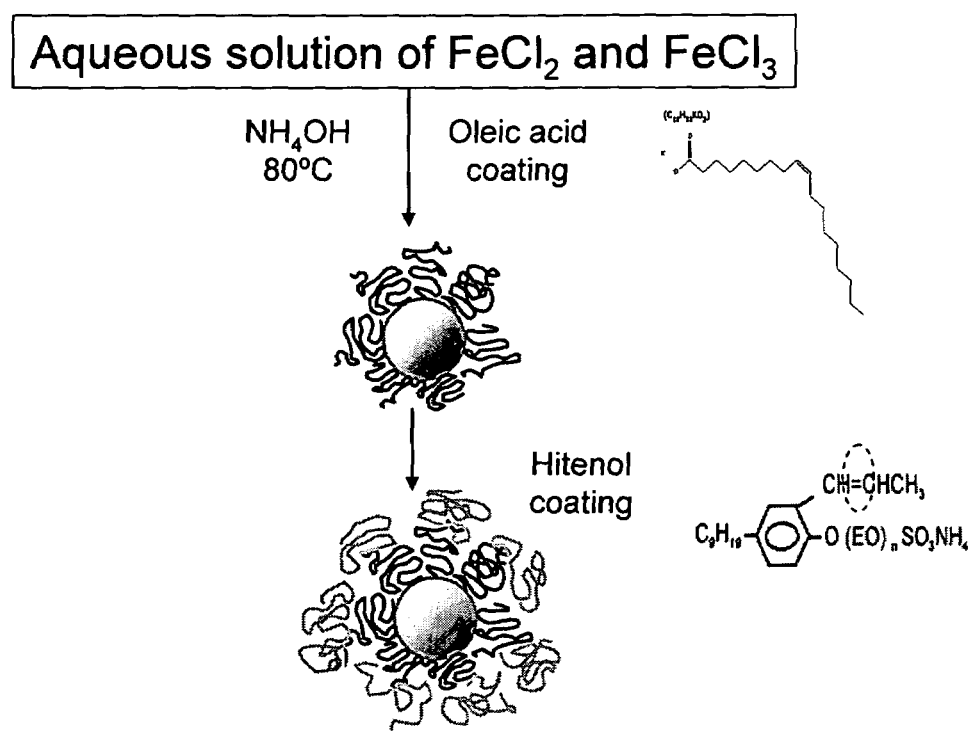
FIG. 22 depicts an embodiment of the present invention where the core is an iron oxide and the hydrocarbon bilayer comprises a oleic acid coating and a Hitenol coating.
Figure 23:
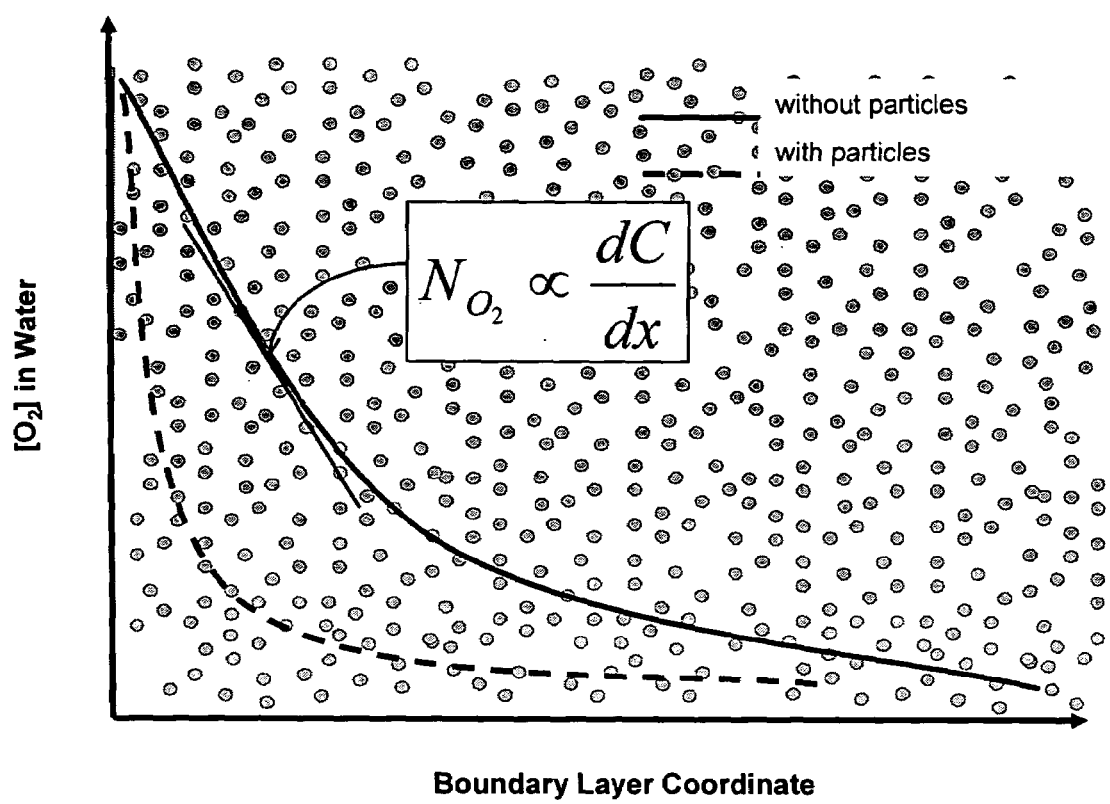
FIG. 23 depicts the initial physical picture for the concentration of $O_2$ in water when the particles are present compared to when they are not.
Figure 24:
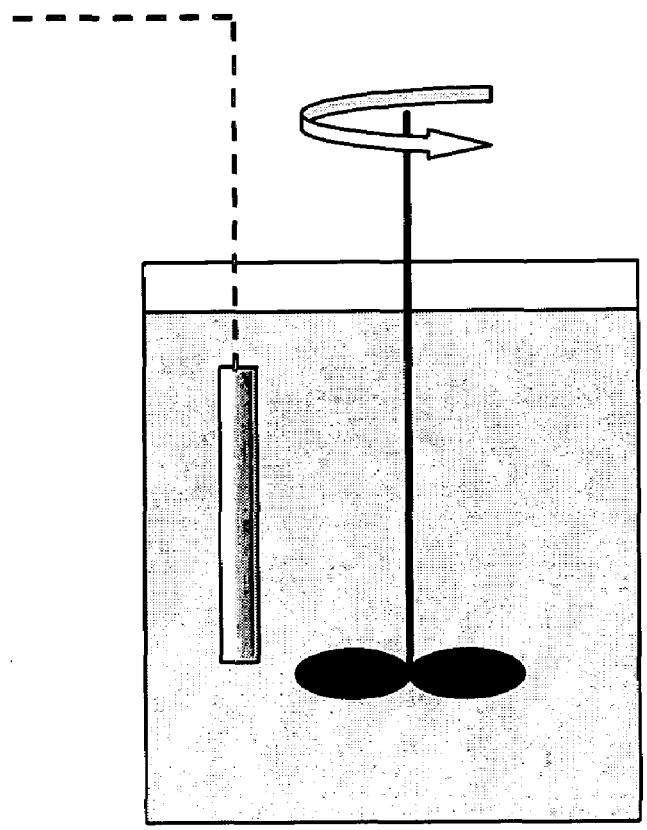
FIG. 24 depicts the experimental setup for mass transfer characterization for an agitated beaker. The setup allows screening of particles for transfer enhancement in a simple system. Advantages of this setup include 1) being able to follow oxygen uptake by surface aeration of an initially purged system, 2) slow kinetics easily followed, and 3) only boundary layer effects; no complications because of possible bubble size and hold-up effects.
Figure 25:
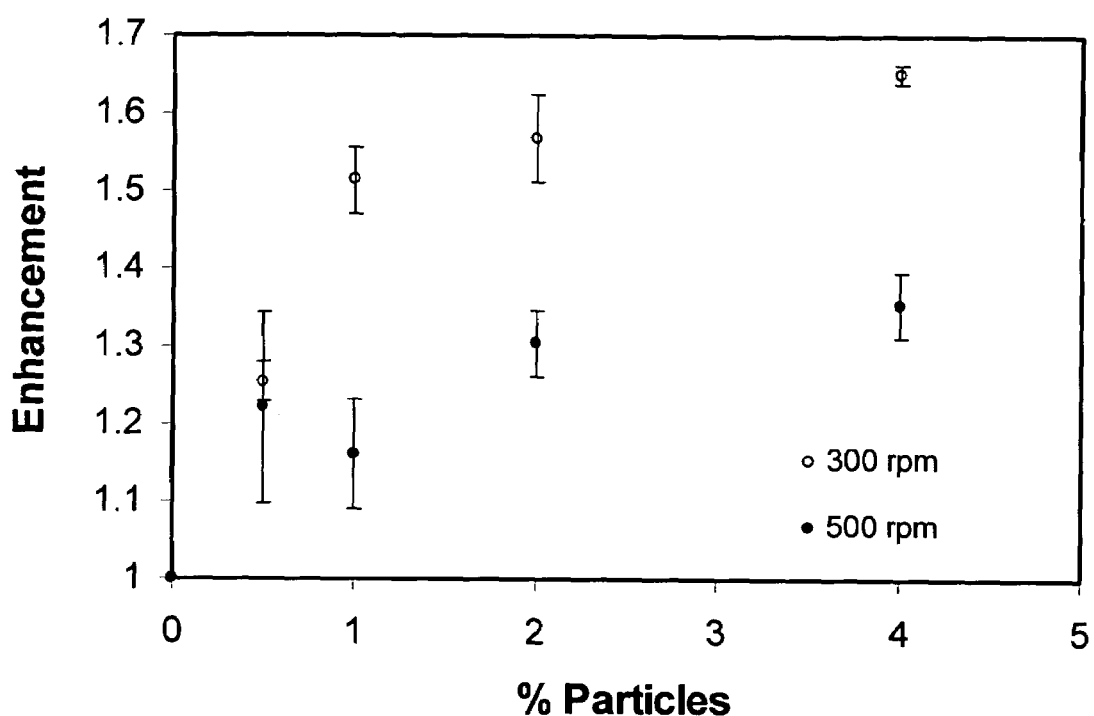
FIG. 25 depicts oxygen enhancement resulting from the particles at various percentages and different RPMs as measured by the formula: Enhancement=$(k_L a)$particles/$(k_L a)$water.
Figure 26:
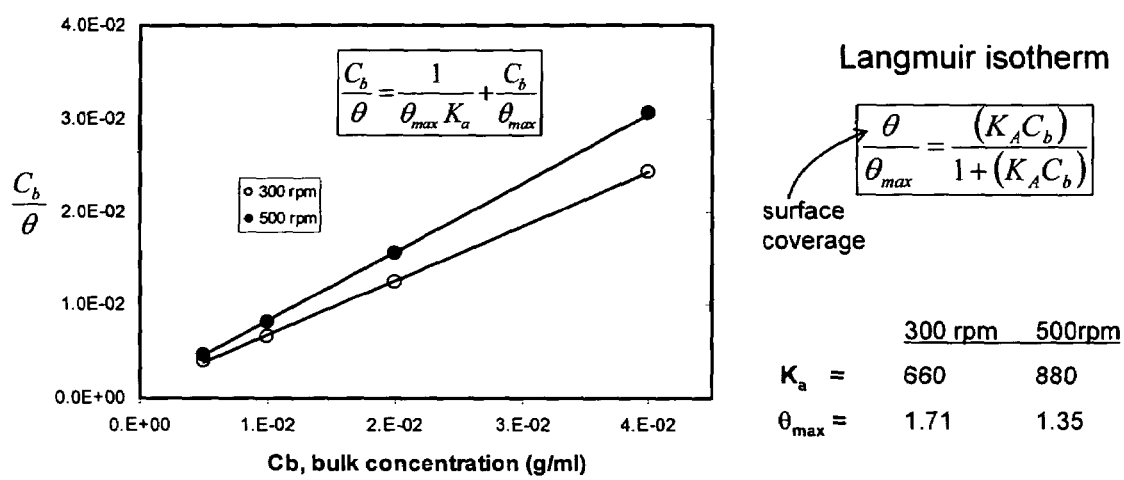
FIG. 26 depicts a fit between an empirical Langmuir-type isotherm and the enhancement data.
Figure 27:
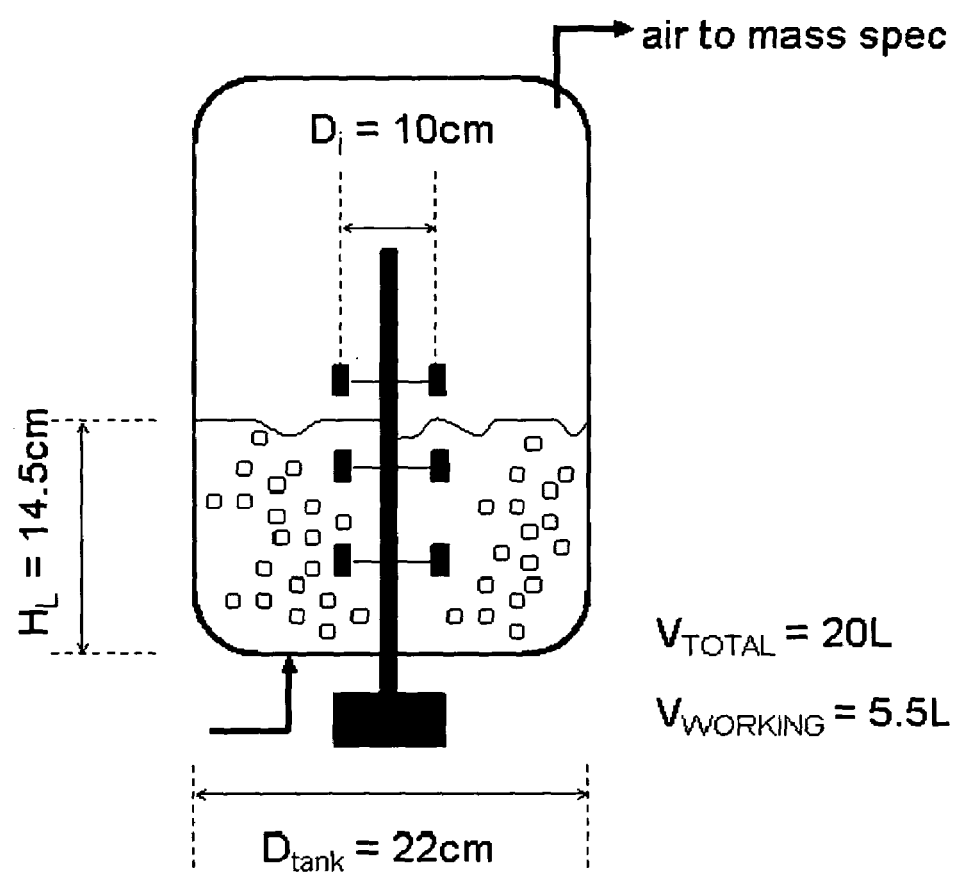
FIG. 27 depicts the experimental setup and various parameters for the mass transfer characterization of the sulfite oxidation method. The sulfite oxidation reaction is described by formula [3]. Oxygen uptake rate was calculated using formula [4]. $[SO_3^{2-}]=0.67$ M and $[Cu^{2+}]=1\times10^{-3}$ M.
Figure 28:
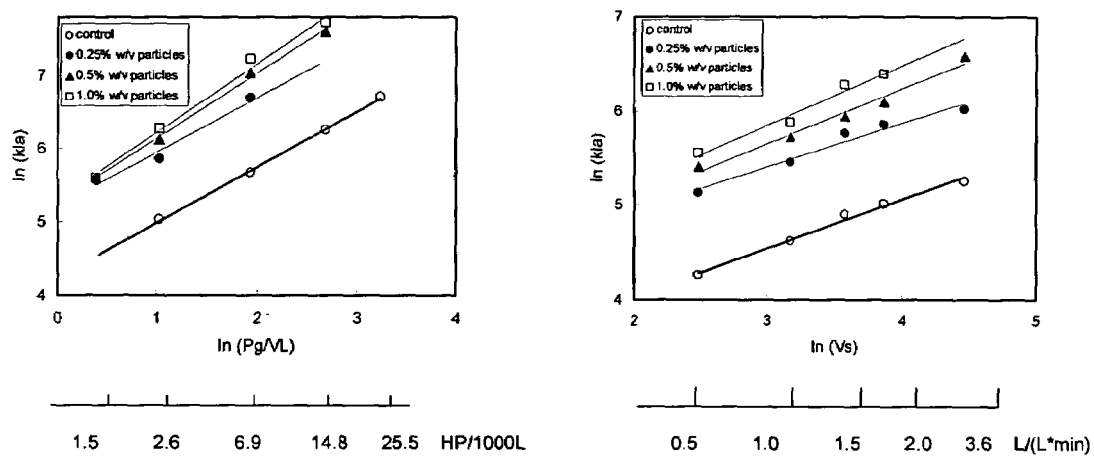
FIG. 28 depicts ln(ka) vs. $\ln(P_g/V_L)$ and ln ($V_s$) for the sulfite oxidation method, wherein $P_g/V_L$ is power input per unit volume, and $V_s$ is superficial velocity.
Figure 29:
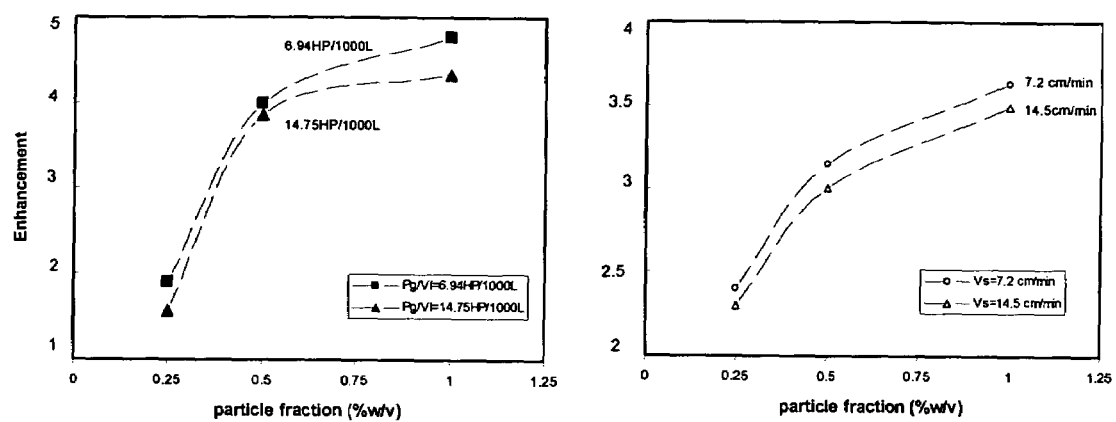
FIG. 29 depicts enhancement at constant superficial velocity and constant power input per unit volume for the sulfite oxidation method.
Figure 30:
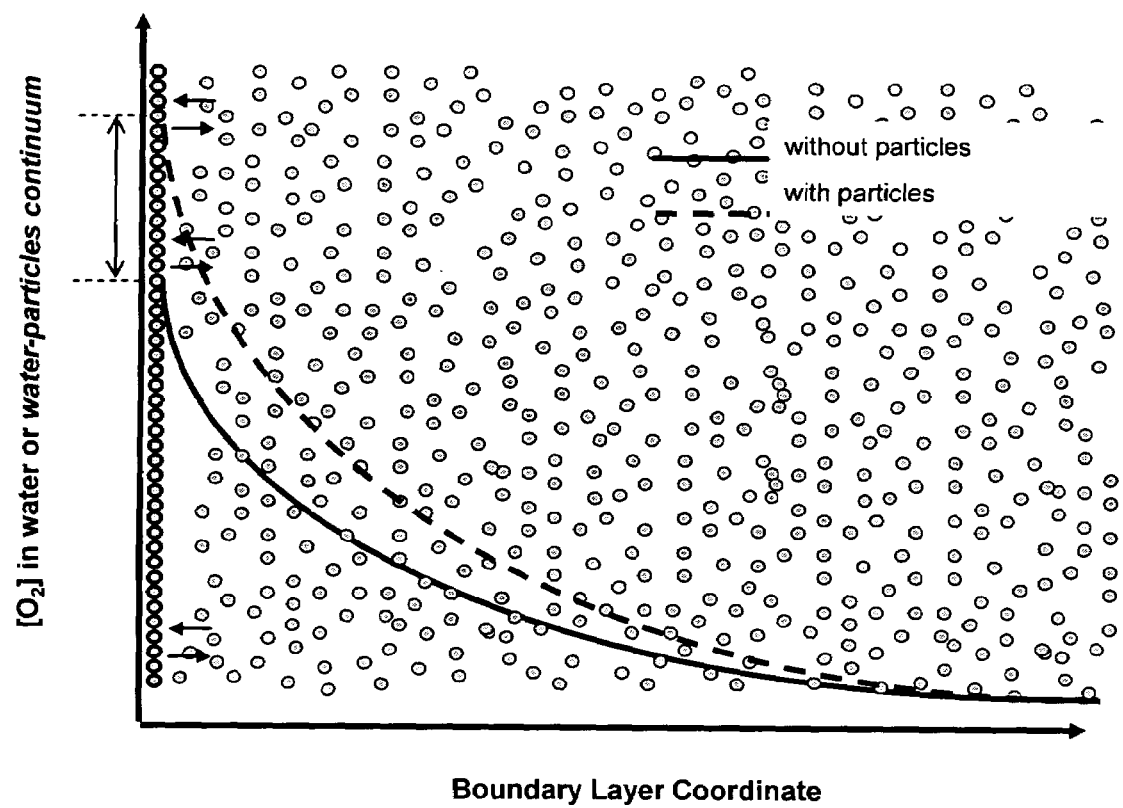
FIG. 30 depicts the proposed enhancement mechanism.
Figure 31:
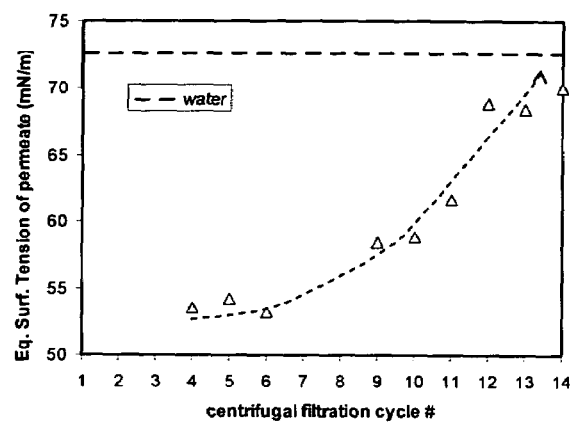
FIG. 31 depicts the method for establishing surface activity of the nanoparticles. The nanoparticles were purified to eliminate all free surfactant by the following method: 1) dialysis for 48 hours (traces of free surfactant still remain), and 2) successive cycles of centrifugal filtration until permeate shows no surface activity.
Figure 31:
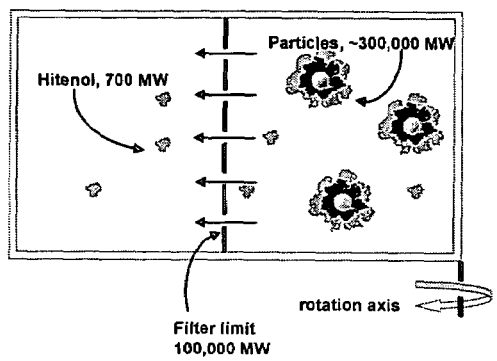
Figure 32:
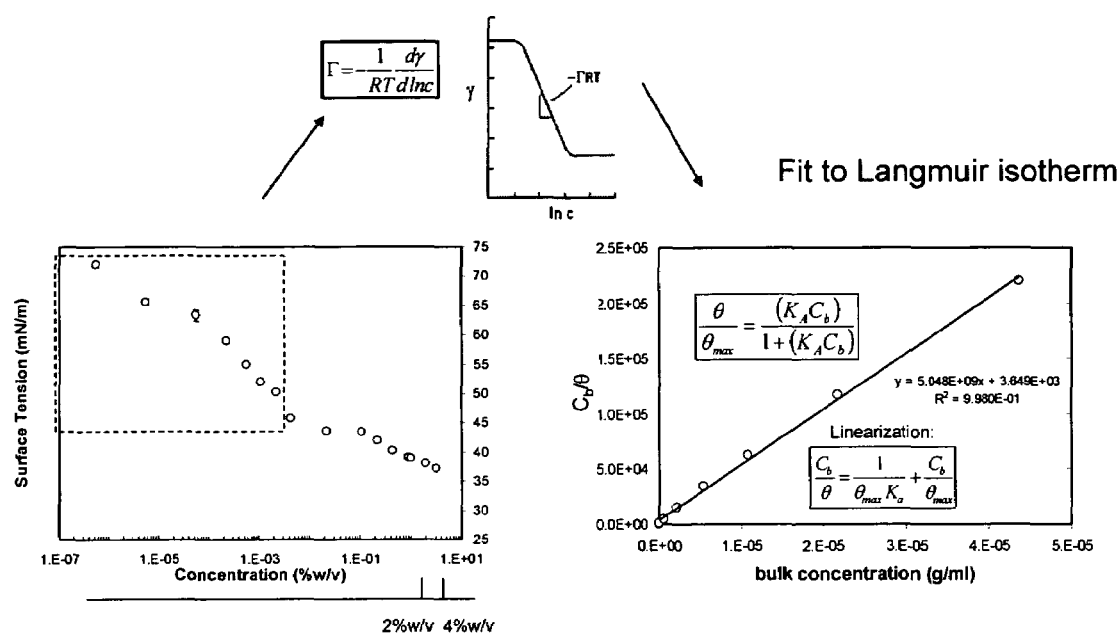
FIG. 32 depicts the method of estimating surface excess properties by measuring concentration dependence of the equilibrium surface tension, and analyzing the data using Gibbs adsorption isotherm.
Figure 33:
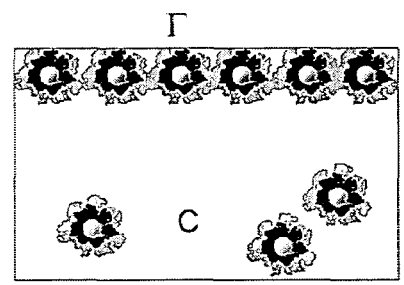
FIG. 33 depicts the calculations for the characteristic time scale for diffusion of the particles to the GL interface.
Figure 34:
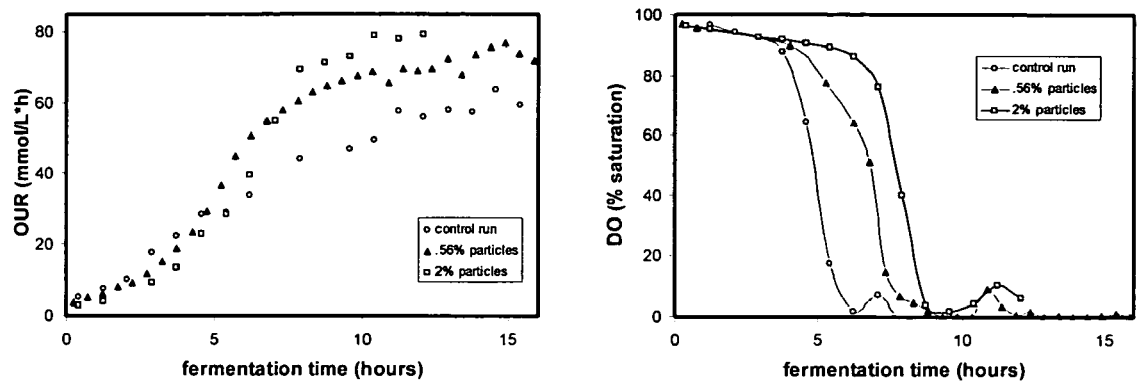
FIG. 34 depicts the *E. coli* fed batch fermentation results.

FIG. 19 illustrates the resulting pH drop due to $CO_2$ sparging for the magnetic nanoparticle solution described above compared versus the pH drop for a control, which consisted of 100 mM NaCl in water, but without magnetic particles. It can be observed that, with the same $CO_2$ flowrate through the system, the change in pH for the magnetic nanoparticle solution is significantly slower.

The slower change in pH can be due to $CO_2$ being preferentially solubilized in the nanoparticles' hydrocarbon coating.

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A nanoparticle comprising an inorganic compound associated with an organic phase, wherein the organic phase is capable of reversibly solubilizing a gas.

2. The nanoparticle of claim 1, wherein the inorganic compound is an inorganic oxide.

3. The nanoparticle of claim 1, wherein the inorganic compound is a transition metal oxide.

4. The nanoparticle of claim 1, wherein the inorganic compound is a Group 8–10 transition metal oxide.

5. The nanoparticle of claim 1, wherein the inorganic compound is a Group 8 transition metal oxide.

6. The nanoparticle of claim 1, wherein the inorganic compound is an iron oxide.

7. The nanoparticle of claim 1, wherein the inorganic compound is $Fe_2O_3$ or $Fe_3O_4$.

8. The nanoparticle of claim 1, wherein the inorganic compound is $Fe_3O_4$.

9. The nanoparticle of claim 1, wherein the nanoparticle is magnetic.

10. The nanoparticle of claim 1, wherein the nanoparticle is non-toxic.

11. The nanoparticle of claim 1, wherein the gas is oxygen.

12. The nanoparticle of claim 1, wherein the gas is $CO_2$.

13. The nanoparticle of claim 1, wherein the inorganic compound is incorporated within the interstices of a fluorine-containing polymer.

14. The nanoparticle of claim 13, wherein the fluorine-containing polymer is a copolymer.

15. The nanoparticle of claim 13, wherein the fluorine-containing polymer is a copolymer comprising a fluorinated moiety and a non-fluorinated moiety.

16. The nanoparticle of claim 13, wherein the gas is oxygen and the fluorine-containing polymer is capable of reversibly binding oxygen in an aqueous medium.

17. The nanoparticle of claim 13, wherein the gas is $CO_2$ and the fluorine-containing polymer is capable of reversibly binding $CO_2$ in an aqueous medium.

18. The nanoparticle of claim 1, wherein the organic phase comprises a first and second hydrocarbon layer chemically bonded to each other.

19. The nanoparticle of claim 18, wherein the first hydrocarbon layer comprises a carbonyl functional group.

20. The nanoparticle of claim 18, wherein the first hydrocarbon layer comprises a fatty acid.

21. The nanoparticle of claim 18, wherein the first hydrocarbon layer comprises oleic acid.

22. The nanoparticle of claim 18, wherein the second hydrocarbon layer comprises a hydrophilic group.

23. The nanoparticle of claim 18, wherein the second hydrocarbon layer comprises a nonionic and an anionic hydrophilic group.

24. The nanoparticle of claim 18, wherein the second hydrocarbon layer comprises a polyoxyalkylene sulfonate moiety.

25. The nanoparticle of claim 18, wherein the second hydrocarbon layer comprises a polyoxyethylene sulfonate moiety.

26. The nanoparticle of claim 18, wherein the first and second hydrocarbon layer are bonded together through a carbon-carbon single bond.

27. The nanoparticle of claim 18, wherein the gas is oxygen and the organic phase is capable of reversibly binding oxygen in an aqueous medium.

28. The nanoparticle of claim 1, wherein the nanoparticle is capable of forming an aqueous colloid.

29. The nanoparticle of claim 1, wherein the nanoparticle has a diameter of about 1 to about 1,000 nm.

30. The nanoparticle of claim 1, wherein the nanoparticle has a diameter of about 10 to about 100 nm.

31. The nanoparticle of claim 1, wherein the gas is oxygen.

32. The nanoparticle of claim 1, wherein the gas is $CO_2$.

33. A composition, comprising the nanoparticle of claim 1.

34. The composition of claim 33, wherein the composition is an aqueous colloid.

35. A method of preparing nanoparticles comprising an inorganic compound incorporated within the interstices of a fluorine-containing polymer comprising:
   a) co-precipitating an inorganic salt in an aqueous solution in the presence of a fluorine-containing polymer; and
   b) sonicating the mixture from step a), and isolating the nanoparticles.

36. A method of preparing nanoparticles comprising an inorganic compound associated with a hydrocarbon bilayer comprising a first hydrocarbon layer chemically bonded to a second hydrocarbon layer comprising:
   a) coprecipitating an inorganic salt in an aqueous solution in the presence of a first hydrocarbon moiety capable of bonding with the inorganic compound, and
   b) reacting the product from step a) with a second hydrocarbon moiety comprising a hydrophilic group, wherein the first hydrocarbon moiety chemically bonds to the second hyrdrocarbon moiety to form the hydrocarbon bilayer.

* * * * *